(12) United States Patent
Bitto et al.

(10) Patent No.: US 7,665,369 B2
(45) Date of Patent: Feb. 23, 2010

(54) MEASURING TRANSDUCER OF VIBRATION-TYPE

(75) Inventors: Enio Bitto, Aesch (CH); Alfred Rieder, Landshut (DE); Christian Schütze, Basel (CH); Michael Fuchs, Eschbach (DE); Wolfgang Drahm, Erding (DE); Michael Wiesmann, Freising (DE)

(73) Assignee: Endress + Hauser Flowtec AG, Reinach (CH)

( * ) Notice: Subject to any disclaimer, the term of this patent is extended or adjusted under 35 U.S.C. 154(b) by 0 days.

(21) Appl. No.: 12/314,972

(22) Filed: Dec. 19, 2008

(65) Prior Publication Data

US 2009/0173169 A1    Jul. 9, 2009

Related U.S. Application Data

(60) Provisional application No. 61/008,321, filed on Dec. 20, 2007.

(30) Foreign Application Priority Data

Dec. 20, 2007    (DE)    ...................... 10 2007 062 3979

(51) Int. Cl.
*G01F 1/84* (2006.01)
(52) U.S. Cl. ................................. 73/861.355
(58) Field of Classification Search ............ 73/861.355, 73/861.356, 861.357
See application file for complete search history.

(56) References Cited

U.S. PATENT DOCUMENTS

| | | | |
|---|---|---|---|
| 5,206,587 A | 4/1993 | Rose | |
| 5,412,276 A | 5/1995 | Van Mensvoort | |
| 5,854,430 A * | 12/1998 | Drahm et al. | 73/861.357 |
| 6,347,293 B1 * | 2/2002 | Cunningham et al. | 702/189 |

(Continued)

FOREIGN PATENT DOCUMENTS

DE    198 56 688 A1    6/1999

(Continued)

*Primary Examiner*—Jewel Thompson
(74) *Attorney, Agent, or Firm*—Bacon & Thomas, PLLC

(57) ABSTRACT

The measuring transducer includes: a measuring tube vibrating, at least at times, and serving for conveying medium to be measured; a counteroscillator, which is affixed to the measuring tube on an inlet-side, to form a first coupling zone, and to the measuring tube on an outlet-side, to form a second coupling zone; at least one oscillation exciter for driving at least the measuring tube; as well as at least one oscillation sensor for registering oscillations at least of the measuring tube. During operation, the measuring tube executes, at least at times and/or at least in part, bending oscillations about an imaginary bending oscillation axis, which imaginarily connects the two coupling zones with one another. The oscillation sensor includes a coil, especially a coil affixed to the counteroscillator, as well as, magnetically coupled with the coil, a permanent magnet, which is placed within a magnet cup composed at least partially of magnetically conductive material and which is held to a cup base, especially a cup base secured to the measuring tube. Additionally, it is provided in the measuring transducer of the invention that a cup wall of the magnet cup, especially an essentially circular-cylindrical and/or tubular, cup wall, especially a cup wall extending essentially in the direction of the counteroscillator, has at least one slit, especially a slit extending at least sectionally in the direction of oscillations of the measuring tube relative to the counteroscillator.

38 Claims, 8 Drawing Sheets

U.S. PATENT DOCUMENTS 6,359,359 B1   3/2002   Miura
6,883,387 B2 *  4/2005   Bitto et al. ............. 73/861.355

FOREIGN PATENT DOCUMENTS

| | | |
|---|---|---|
| EP | 0 685 712 A1 | 12/1995 |
| EP | 1 785 697 A1 | 5/2007 |
| EP | 1 985 975 A2 | 10/2008 |
| GB | 2 199 147 A | 6/1988 |
| WO | WO 2007/043996 A1 | 4/2007 |
| WO | WO 2007/057385 A1 | 5/2007 |

* cited by examiner

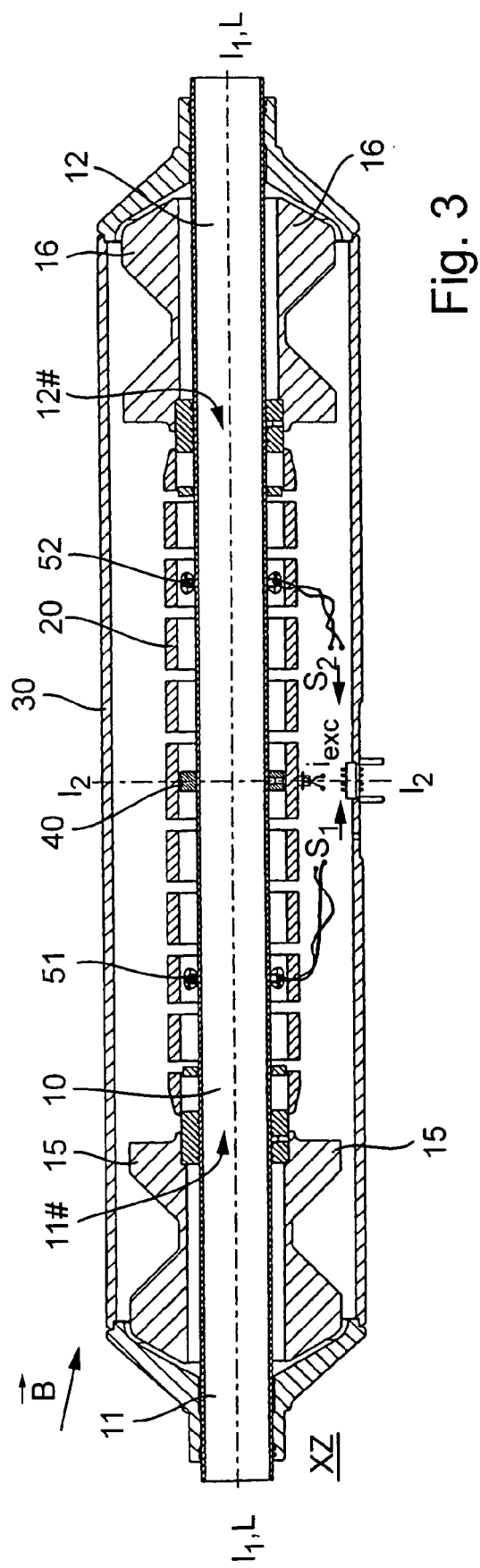
Fig. 3
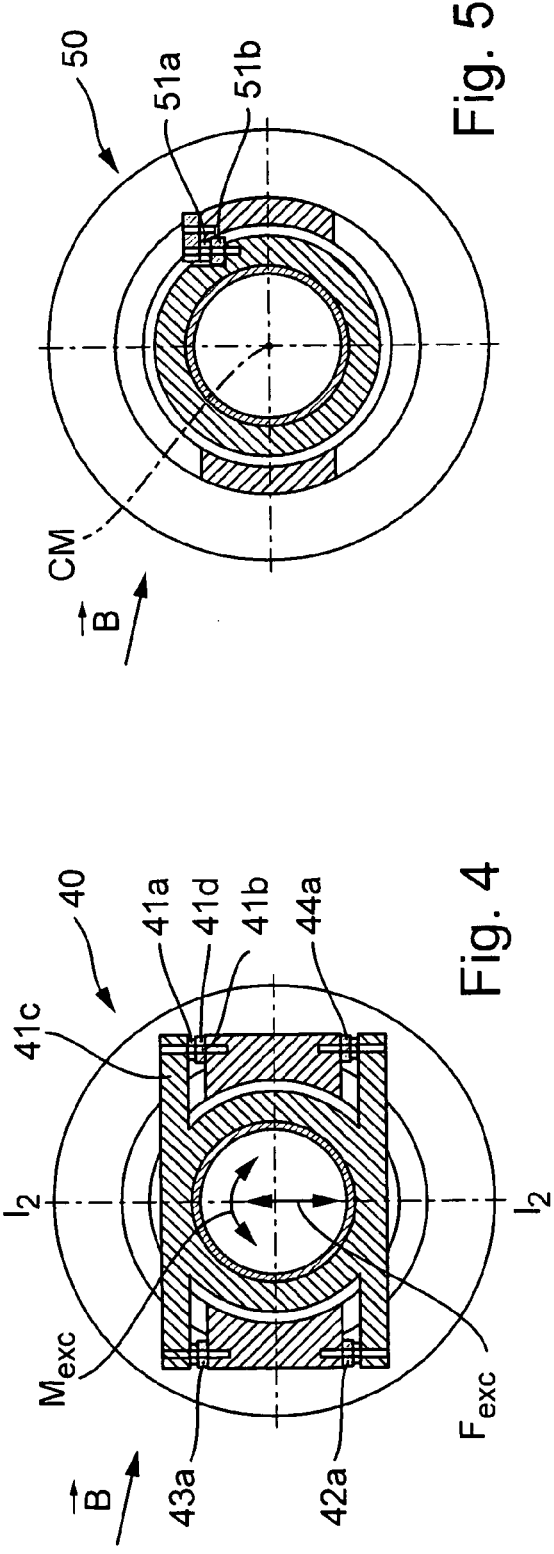
Fig. 5
Fig. 4

MEASURING TRANSDUCER OF VIBRATION-TYPE

CROSS-REFERENCE TO RELATED APPLICATION

This application is a Nonprovisional application which claims the benefit of U.S. Provisional Application Ser. No. 61/008,321, filed on Dec. 20, 2007.

FIELD OF THE INVENTION

The invention relates to a measuring transducer of vibration-type, especially a measuring transducer suited for application in a Coriolis mass flow meter. The measuring transducer includes: At least one measuring tube, vibrating at least at times, for conveying medium to be measured; a counteroscillator, which is affixed to the measuring tube on an inlet side of the measuring tube to form a first coupling zone and at an outlet side of the measuring tube to form a second coupling zone; an exciter mechanism for driving at least the measuring tube; and a sensor arrangement for registering oscillations at least of the measuring tube.

BACKGROUND OF THE INVENTION

Often used in industrial measurements technology, especially in connection with control and monitoring of automated, technical processes, for ascertaining characteristic process parameters, for example a mass flow, a density, a viscosity, etc., of media flowing in a pipeline, for example liquids and/or gases, are in-line measuring devices, especially in-line measuring devices in the form of mass flow meters, which, by means of a measuring transducer of vibration-type and an operating and evaluating electronics connected thereto, induce forces in the flowing medium, for example Coriolis forces, and derived from these, produce a measurement signal measurement signal representing at least one parameter. Such in-line measuring devices having a measuring transducer of vibration-type are long known and well established in industrial usage. Examples of such measuring transducers, especially also their application in Coriolis mass flow meters, are described e.g. in EP-A 317 340, U.S. Pat. No. 4,738,144, U.S. Pat. No. 4,777,833, U.S. Pat. No. 4,823,614, U.S. Pat. No. 5,291,792, U.S. Pat. No. 5,398,554, U.S. Pat. No. 5,476,013, U.S. Pat. No. 5,602,345, U.S. Pat. No. 5,691,485, U.S. Pat. No. 5,796,010 U.S. Pat. No. 5,796,012, U.S. Pat. No. 5,945,609, U.S. Pat. No. 5,979,246, U.S. Pat. No. 6,330,832, U.S. Pat. No. 6,397,685, U.S. Pat. No. 6,691,583, U.S. Pat. No. 6,840,109, U.S. Pat. No. 6,883,387, U.S. Pat. No. 7,077,014, U.S. Pat. No. 7,017,424, U.S. Pat. No. 7,299,699, US-A 2007/0186685, US-A 2007/0151371, US-A 2007/0151370, US-A 2007/0119265, US-A 2007/0119264, WO-A 99 40 394, WO-A 01 02 816 or WO-A 00 14 485. Each of the measuring transducers shown therein includes at least one, essentially straight, or at least one curved, measuring tube, which vibrates during operation and serves for conveying the medium. The measuring tube communicates with the pipeline via an inlet tube piece on the inlet side of the measuring tube and an outlet tube piece on the outlet side of the measuring tube.

Additionally, each of the disclosed measuring transducers includes at least one tubular, box-shaped or plate-shaped counteroscillator, which is embodied as one piece or multi-piece, coupled to the measuring tube on the inlet side to form a first coupling zone and on the outlet side to form a second coupling zone, and likewise caused to vibrate, at least in part, during operation. In the case of the measuring transducers shown in U.S. Pat. No. 5,291,792, U.S. Pat. No. 5,796,010, U.S. Pat. No. 5,945,609, U.S. Pat. No. 7,077,014, US-A 2007/0119262, WO-A 01 02 816 or also WO-A 99 40 394 having a single, essentially straight, measuring tube, such tube and the counteroscillator are, as quite usual in the case of conventional, industrial-grade measuring transducers, directed essentially coaxially with one another. Moreover, in the case of commonly marketed measuring transducers of the aforementioned kind, also the counteroscillator is, most often, essentially tubular and essentially straight and, additionally, arranged in the measuring additionally, arranged in the measuring transducer in such a manner that the measuring tube is at least partially surrounded by the counteroscillator, and such that measuring tube and counteroscillator are essentially coaxially directed. Materials used for such counteroscillators include, among others, comparatively cost-favorable steel types, such as, perhaps, structural steel or free-machining steel.

Measuring transducers of the kind discussed here include, additionally, an exciter mechanism, which, driven by an appropriately conditioned, electrical driver signal, excites the measuring tube during operation by means of at least one electromechanical, especially electrodynamic, oscillation exciter to execute bending oscillations, usually, as much as possible, predominantly or exclusively, in a single, imaginary, tube oscillation plane, hereinafter referred to as the primary plane of oscillation and imaginarily passing through the two coupling zones. Additionally, such measuring transducers include a sensor arrangement having oscillation sensors, especially electrodynamic oscillation sensors, for the at least pointwise registering of inlet-side and outlet-side oscillations of the measuring tube and for producing electrical, sensor signals influenced by the mass flow.

The exciter mechanism includes at least one electrodynamic, oscillation exciter and/or an oscillation exciter differentially acting on measuring tube and counteroscillator, while the sensor arrangement includes an inlet-side, most often likewise electrodynamic, oscillation sensor, as well as an outlet-side, oscillation sensor of essentially equal construction. In the case of usually marketed measuring transducers having a single measuring tube and a counteroscillator coupled thereto, the oscillation exciter is formed usually by means of a coil, through which an electrical current flows, at least at times, and through which a magnetic field passes, at least at times, as well as by means of a rather elongated, especially rod-shaped, permanent magnet serving as armature, interacting with, especially plunging in, the at least one coil, and being appropriately affixed to the measuring tube. Permanent magnet and coil are, in such magnet and coil are, in such case, usually so oriented that they extend essentially coaxially with respect to one another.

Additionally, in the case of conventional measuring transducers, the exciter mechanism is usually constructed and placed in the measuring transducer in such a manner that it acts essentially centrally on the measuring tube. Most often, the at least one oscillation exciter and, as a result, the exciter mechanism, is, in such case, additionally, as shown, for example, also in the measuring transducers disclosed in U.S. Pat. No. 5,796,010, U.S. Pat. No. 6,840,109, U.S. Pat. No. 7,077,014 or U.S. Pat. No. 7,017,424, affixed externally to the measuring tube, at least pointwise along an imaginary, central, peripheral line thereof. Alternatively to an exciter mechanism formed by means of oscillation exciters acting rather centrally on the measuring tube, for example, as proposed in, among others, U.S. Pat. No. 4,823,614, an exciter mechanism can be applied, which is formed by means of two oscillation exciters affixed to the measuring tube, not in the center of thereof, but instead more toward the inlet and outlet ends thereof.

In the case of most measuring transducers of the described kind, the oscillation sensors of the sensor arrangement are, as already indicated, constructed according to the same principle, at least to the extent that they are embodied with essentially equal construction as the at least one oscillation exciter. Accordingly, also the oscillation sensors of such a sensor arrangement are formed, most often, in each case, by means of at least one coil usually affixed to the counteroscillator. At least at times, a varying magnetic field also passes through this coil and, associated therewith, the coil bears, at least at times, an induced, measurement voltage. Additionally, these oscillation sensors each also include a permanently magnetic armature, which is affixed to the measuring tube. interacts with the at least one coil, and supplies the magnetic field. Each of the aforementioned coils is, additionally, connected by at least one pair of electrical connection lines with the mentioned operating- and evaluating-operating- and evaluating-electronics of the in-line measuring device. The connection lines are, most often, guided on the shortest possible path from the coils, along the counteroscillator, to the transducer housing.

For homogenizing the magnetic field passing through coils and permanent magnets, as well as for preventing disturbing stray fields, oscillation sensors of the aforementioned kind as well as also most oscillation exciters have the permanent magnet placed within a magnet cup made at least partially of magnetically conductive material. The permanent magnet is mounted there to a cup base usually directly secured to the measuring tube. Extending from the cup base in the direction of the relative oscillations of measuring tube and counteroscillator is a tubular, essentially circularly cylindrical, cup wall of the magnet cup. Usually, the permanent magnet is arranged essentially in a center of the cup base and, most often, so affixed thereto that permanent magnet and cup wall are oriented to extend essentially coaxially with one another.

Besides the oscillation sensors provided for registering vibrations of the measuring tube, the measuring transducer can, as also proposed, among other things, in EP 831 306, U.S. Pat. No. 5,736,653, U.S. Pat. No. 5,381,697 or WO-A 01/02 816, include still other sensors arranged on the inner part formed, in any case, by means of measuring tube, counteroscillator, as well as the exciter mechanism and sensor arrangement, provided, in each case, thereon or also in their proximity, and serving especially for registering rather secondary measured variables, such as e.g. temperature, acceleration, strain, stress, etc.

Finally, each of the measuring transducers shown in U.S. Pat. No. 5,291,792, U.S. Pat. No. 5,945,609, U.S. Pat. No. 7,077,014, US-A 2007/0119264, WO-A 01 02 816 or also WO-A 99 40 394 includes an extra, transducer housing surrounding the measuring tube, with counteroscillator coupled thereto, as well as the provided exciter mechanism and and sensor arrangement, especially such a transducer housing affixed directly to the inlet tube piece and to the outlet tube piece, while, for example, in the case of the measuring transducer shown in U.S. Pat. No. 4,823,614, the transducer housing is formed quasi by the counteroscillator, or, in other words, transducer housing and counteroscillator are one and the same component.

An advantage of measuring tranducers with straight measuring tube, in comparison to those with curved, or angled, measuring tube, is e.g. that the straight measuring tube empties, to a high degree of certainty, in almost any installed orientation, especially also following an in-line-conducted cleaning. Additionally, such measuring tubes are significantly easier and accordingly more cost favorable to manufacture, as compared e.g. to a curved measuring tube, while, in operation, they, most often, result in a lesser pressure drop.

A straight measuring tube, as is known, brings-about Coriolis forces, when it is excited to execute bending oscillations in the primary oscillation plane according to a first form of eigenoscillation—the so-called drive-mode, or also, wanted-mode. In the case of conventional measuring transducers of the aforementioned type, for example also those disclosed in U.S. Pat. No. 5,291,792, U.S. Pat. No. 6,840,109, U.S. Pat. No. 7,077,014 or U.S. Pat. No. 7,017,424, when the measuring tube is caused to oscillate in the wanted mode mainly in the imaginary, primary plane of oscillation, these Coriolis forces lead, in turn, to the fact that, superimposed on the same bending oscillations in the wanted mode are coplanar (thus, executed likewise in the primary plane of oscillation) bending oscillations according to a second form of eigenoscillation of, most often, higher order, in any case, however, of other symmetry characteristics (the so-called Coriolis-, or also, measuring-mode). As a result of the bending oscillations in the Coriolis mode, the oscillations registered inlet-side and outlet-side by means of the sensor arrangement exhibit a measurable phase difference dependent also on mass flow.

Usually, the measuring tubes of such measuring transducers, especially those utilized in Coriolis mass flow meters, are excited in the wanted mode to an instantaneous resonance frequency of a first form of eigenoscillation, especially at oscillation amplitude controlled to be constant. Since this resonance frequency depends, especially, also on the instantaneous density of the medium, at least also the density of flowing media can be directly measured by means of usually marketed Coriolis, mass flow meters.

Besides the above-mentioned, more or less marked density-dependence, a special problem of measuring transducers as above described with straight measuring tube lies, however, therein (and this is also discussed, for example, in U.S. Pat. No. 5,291,792, U.S. Pat. No. 7,077,014 or the not-pre-published, German patent application 102007050686.6 of the assignee), that they exhibit not only the above-discussed, natural modes of oscillation, in which the measuring tube executes bending oscillations in the mentioned, primary plane of oscillation, but also natural modes of oscillation, in which the measuring tube can execute bending oscillations in another imaginary, secondary plane of oscillation essentially orthogonal to the primary plane of oscillation and equally imaginarily cutting through the two coupling zones, and that, without the accessing of special measures, these modes of oscillation in the secondary plane of oscillation can naturally exhibit about the same resonance frequency as possessed by the respectively corresponding mode of oscillation in the primary plane of oscillation. In other words, in the case of measuring transducers of the type being discussed, with straight measuring tube, possible inaccuracies of measurement, especially based on changes of the zero-point unpredictable during operation, can result from the fact that, in addition to the desirably excited, wanted mode in the primary plane of oscillation, undesired and, thus, disturbing oscillations occur in the secondary plane of oscillation and lie close to the frequencies of oscillation of the wanted mode. Equally as for the wanted mode in the primary plane of oscillation, there would then also be induced, for the equal-frequency modes of oscillation in the secondary plane of oscillation excited in undesired manner, additional in undesired manner, additional modes of oscillation coplanar therewith, related to corresponding Coriolis forces. A cause of such disturbances can be, for example, vibrations in the connected pipeline or, also, most-often broadband noise stemming from the flowing medium. As a result of, in practice, almost unavoidable, transverse sensitivities of the oscillation sensors to oscillations in the secondary plane of oscillation, this leads to the fact that the sensor signals delivered under such circumstances reflect, in part, both oscillations of the measuring tube in the primary plane of oscillation as well as also corresponding oscillations of the measuring tube in the secondary plane of oscillation, to a degree significant for accuracy of measurement. A matching of the corresponding signal parts to the primary and secondary planes of oscillation is, practically, not possible, because the oscillations have essentially equal frequencies. Moreover, in the case of sufficiently strong, mechanical coupling of the oscillatory modes of the two planes of oscillation, also a transfer of oscillatory energy is possible, spontaneously or periodically, from the primary into the secondary plane of oscillation, or also the other way around, from the secondary into the primary plane of oscillation.

As a result of this, the sensor signals can exhibit, for example, a characteristic beat quite damaging both for their signal processing as well as also for oscillation control based on the sensor signals. Furthermore, oscillatory motions in the secondary plane of oscillation, be they excited directly by external disturbances or indirectly via the aforementioned energy transfer from the primary into the secondary plane of oscillation, can lead to the fact that the sensor signals can exhibit an, at times, overly high signal level, with the result that the input amplifier receiving and processing the sensor signals must be, correspondingly, over dimensioned and, consequently, comparatively expensive.

For suppressing such, on the whole, very damaging oscillations executed in the secondary plane of oscillation, it is usual to increase a stiffness of the measuring tube effective for these oscillations relative to a stiffness of the measuring tube effective for oscillations in the primary plane of oscillation, while keeping effective masses essentially equal, and, so, to effectively separate from one another, resonance frequencies of corresponding modes of oscillation of primary and secondary planes of oscillation. Typically, in such case, frequency separations of more than 30 Hz are sought. In U.S. Pat. No. 5,602,345, for this, it is proposed, for example, to apply spring elements in the form of flat struts placed additionally on the particular measuring tube on the inlet and outlet sides in the immediate vicinity of the respective coupling zones. A further possibility for separating oscillation modes in the primary plane of oscillation from corresponding modes of oscillation in the secondary plane of oscillation is additionally disclosed in U.S. Pat. No. 5,291,792. In the measuring transducer proposed there, the stiffness of the measuring tube effective for oscillations in the secondary plane of oscillation is increased by biasing the measuring tube at its center with a correspondingly acting, spring element in the form of an, in such case, U-shaped, stiffening spring arranged extending in the measuring transducer essentially in radial direction to measuring tube and counteroscillator. This spring element does not influence the stiffness of the measuring tube for the Coriolis mode in the primary plane of oscillation to any extent worth mentioning. In this way, it is possible to achieve that the oscillation frequency of oscillations in the wanted mode rises sufficiently strongly above the frequency of undesired, thus disturbing, oscillations, so that the influence of such disturbing oscillations is largely suppressed. Alternatively to this, in the mentioned German patent application 1020070500686.6, it has been proposed to use "decentralized" spring elements placed on the inlet and outlet sides in the vicinity of the coupling zones for frequency separation.

As discussed in the non-prepublished, German patent applications 102006062220.0, 102006062219.7, or 102006062185.9 of the assignee, it has additionally been possible—especially also in the case of an inner part perfectly balanced as regards density, at least under laboratory conditions, and caused to oscillate solely in the primary oscillation plane—to identify the connection lines as a further source for such disturbances of the oscillation measurement signals, especially disturbances affecting also the zero point. Taking this into account, it is proposed in these patent applications to counteract such disturbances by a specially suited leading of the lines along the inner part, out to the transducer housing.

Although the aforementioned measures, taken singly or in combination, have led to quite significant improvements of the measuring accuracy of measuring transducers of the type being discussed, especially also as regards their zero point stability, further investigations, especially investigations carried out also under laboratory conditions and largely free of disturbing vibrations have still led to the detection of fluctuations in the zero point, which, although small, are nevertheless not insignificant for the extremely high accuracy of measurement sought-after for such measuring transducers, and it has not been possible to explain these fluctuations on the basis of any of the above-mentioned phenomena. Especially, it has been found that, despite extensive elimination or prevention of the above-mentioned disturbances, still there is a certain dependence of the zero point on the installation situation, which, in turn, shows a certain dependence on location.

Other disturbance sources potentially degrading the measuring accuracy, especially the stability of the zero point, of measuring transducers of the type discussed, sources such as electromagnetic, alternating fields, or, as discussed, among others, in U.S. Pat. No. 7,299,699, oscillatory rubbing, material fatigue, or loosening of component connections, could, in such case, likewise, be eliminated or would not be able to explain at least the degree of the observed shiftings of the zero point.

Laboratory experiments with a Helmholtz coil, involving exposing a measuring transducer of the type being discussed, installed in various positions, to the switched magnetic field (known to be largely homogeneous) of the Helmholtz coil have finally, surprisingly, identified constant magnetic fields as a possible disturbance source for the long inexplicable, high, observed shiftings of the zero point. Taking this further, it was, thus, finally possible to discover also the special influence of the earth's magnetic field, which is location-dependent, in the above sense, to a considerable degree, as the cause for a locational dependence of the zero point, or, much more, a locational dependence of its changes. Considering the rather high field strengths of about 800 mT, which bring-about the regular measuring voltages in the oscillation sensors, and in view of the fact that the earth's magnetic field is weaker by some orders of magnitude, the sensitivity of the oscillation sensors to local changes of the earth's magnetic field density is quite surprising.

Now, a possibility for removing the aforementioned problem would be available, for example, in the direction of so constructing the transducer housing that its effective magnetic resistance is significantly lessened. This, in turn, would require the use of materials having a comparatively high, relative magnetic conductivity, such as free-machining steel or structural steel. However, such materials can, as discussed, for example, also in U.S. Pat. No. 6,330,832, not always completely satisfy the high requirements placed on industrial-grade, measuring transducers of the type being discussed, as regards corrosion resistance and/or hygiene, so that then measures would have to be utilized further increasing the anyway already high materials- and/or manufacturing-complexity.

SUMMARY OF THE INVENTION

An object of the invention is to improve measuring transducers of the aforementioned kind such that a markedly smaller dependence of the measuring accuracy on the actual installed position and/or the actual location of installation of the measuring transducer can be reached. This should be achieved, especially while maintaining, in comparison with conventional measuring transducers, comparable or only insignificantly higher complexity as regards manufacture and/or material.

For achieving the object, the invention resides in a measuring transducer of vibration-type for a medium flowing in a pipeline. The measuring transducer includes: A measuring tube vibrating, at least at times, and serving for conveying medium to be measured; a counteroscillator, which is affixed to the measuring tube on its inlet side for forming a first coupling zone and to the measuring tube on its outlet side for forming a second coupling zone; at least one oscillation exciter, especially an electrodynamic oscillation exciter, for producing, for example differentially, mechanical oscillations at least of the measuring tube relative to the counteroscillator; as well as at least a first oscillation sensor, especially an electrodynamic oscillation sensor, for registering, for example differentially, oscillations at least of the measuring tube relative to the counteroscillator. In the case of the measuring transducer of the invention, the at least one oscillation sensor includes a coil, for example a coil affixed to the counteroscillator, as well as a permanent magnet magnetically coupled with the coil and placed within a magnet cup composed at least partially of magnetically conductive material. The permanent magnet is held to a cup base, and the cup base is, in turn, secured, for example, to the measuring tube. Moreover, in the case of the measuring transducer of the invention, it is provided that a cup wall of the magnet cup, formed tubularly and/or, for example, essentially circular-cylindrically, and extending from the cup base, for example, essentially in the direction of the counteroscillator example, essentially in the direction of the counteroscillator and/or in the direction of bending oscillations of the measuring tube relative to the counteroscillator, has at least one slit extending, for example, at least sectionally, in the direction of oscillations of the measuring tube relative to the counteroscillator.

Beyond this, the invention resides in an in-line measuring device, for example one embodied as a Coriolis mass flow measuring device, density measuring device, viscosity measuring device, or the like, for measuring and/or monitoring at least one parameter, for example a mass flow, e.g. mass flow rate, a density and/or a viscosity of a medium flowing in a pipeline, in which in-line measuring device a measuring transducer of the above-defined kind is applied.

The measuring transducer is, especially, further so embodied that it has at least a first, natural mode of oscillation, in which at least the measuring tube can execute bending oscillations in an imaginary, primary plane of oscillation. Developing this aspect of the measuring transducer of the invention further, it is provided that the measuring tube is excited, at least at times during operation, by means of the at least one oscillation exciter in such a manner that it oscillates, at least partially, especially predominantly or exclusively, in the imaginary, primary plane of oscillation.

In a first embodiment of the invention, it is provided that the coil of the oscillation sensor is affixed to the counteroscillator.

In a second embodiment of the invention, it is provided that the permanent magnet of the at least one oscillation sensor is mechanically coupled with the measuring tube.

In a third embodiment of the invention, it is provided that the cup base of the magnet cup of the at least one oscillation sensor is secured to the measuring tube.

In a fourth embodiment of the invention, it is provided that the permanent magnet, which is, for example, elongated and/or rod-shaped, and the coil of the at least one oscillation sensor are directed essentially extending coaxially with one another.

In a fifth embodiment of the invention, it is provided that the permanent magnet of the at least one oscillation sensor and the cup wall are directed essentially coaxially extending relative to one another.

In a sixth embodiment of the invention, it is provided that the permanent magnet of the at least one oscillation sensor is affixed to the cup base essentially in a center thereof.

In a seventh embodiment of the invention, it is provided that the permanent magnet of the at least one oscillation sensor and the at least one slit are directed at least sectionally, for example, predominantly or entirely, extending essentially parallel to one another.

In an eighth embodiment of the invention, it is provided that the at least one slit is, at least sectionally, for example predominantly or entirely, essentially straight.

In a ninth embodiment of the invention, it is provided that the at least one slit extends at least to the floor of the cup.

In a 10th embodiment of the invention, it is provided that the at least one slit extends to a free edge of the magnet cup, for example a free edge facing essentially the counteroscillator. Developing this embodiment of the invention further, it is provided that the at least one slit extends, starting from the free edge of the magnet cup facing, for example, the counteroscillator, along the cup wall, at least to the cup base.

In an 11th embodiment of the invention, it is provided that also the cup base is slit.

In a 12th embodiment of the invention, it is provided that the at least one slit extends at least sectionally along the cup base, for example in the direction of a radius of the cup base.

In a 13th embodiment of the invention, it is provided that also the permanent magnet of the at least one oscillation sensor is at least sectionally slit.

In a 14th embodiment of the invention, it is provided that also the permanent magnet of the at least one oscillation sensor has at least one slit, for example a slit extending at least sectionally in the direction of oscillations of the measuring tube relative to the counteroscillator. Developing this embodiment of the invention further, it is additionally provided that the at least one slit extends to a free edge of the permanent magnet essentially facing the counteroscillator.

In a 15th embodiment of the invention, it is provided that the measuring tube is composed, at least partially, for example predominantly or completely, of a material, which has a smaller magnetic conductivity than a material of which the counteroscillator is at least predominantly composed.

In a 16th embodiment of the invention, it is provided that the counteroscillator is composed at least partially, for example predominantly or completely, of a magnetically conductive material.

In a 17th embodiment of the invention, it is provided that the counteroscillator is composed at least partially, for example predominantly or completely, of a magnetically conductive material having a relative permeability of at least 10, for example more than 100.

In an 18th embodiment of the invention, it is provided that the counteroscillator is composed at least partially, for example predominantly or completely, of a steel, e.g. a free-machining steel or a structural steel.

In a 19th embodiment of the invention, it is provided that the permanent magnet of the at least one oscillation sensor is composed at least partially, for example predominantly or completely, of a rare earth alloy, such as e.g. AlNiCo, NyFeB, SmCo or the like.

In a 20th embodiment of the invention, it is provided that the permanent magnet of the at least one oscillation sensor is composed at least partially, for example predominantly or completely, of ferrite.

In a 21st embodiment of the invention, it is provided that the magnet cup of the at least one oscillation sensor is composed at least partially, for example predominantly or completely, of a steel, such as e.g. a free-machining steel or a structural steel.

In a 22nd embodiment of the invention, it is provided that the magnet cup of the at least one oscillation sensor is composed at least partially, for example predominantly or completely, of ferrite.

In a 23rd embodiment of the invention, it is provided that the counteroscillator is composed at least partially, for example predominantly or completely, of steel, such as e.g. free-machining steel or structural steel.

In a 24th embodiment of the invention, it is provided that the measuring tube is composed, at least partially, for example predominantly or completely, of steel, for example stainless steel and/or austenitic steel, such as e.g. 316 L, 318 L, or nickel alloy, such as e.g. Hastelloy.

In a 25th embodiment of the invention, it is provided that the measuring tube is composed at least partially, for example predominantly or completely, of titanium.

In a 26th embodiment of the invention, it is provided that the measuring tube is composed at least partially, for example predominantly or completely, of tantalum.

In a 27th embodiment of the invention, it is provided that the measuring tube is composed at least partially, for example predominantly or completely, of zirconium.

In a 28th embodiment of the invention, it is provided that the magnet cup of the at least one oscillation sensor has at least two slits, for example also a plurality thereof and/or slits extending essentially parallel to one another at least within the cup wall and/or which are essentially uniform, at least within the cup wall.

In a 29th embodiment of the invention, it is provided that the magnet cup of the at least one oscillation sensor has at least two slits, for example also a plurality thereof, extending, for example, essentially radially within the cup base and/or essentially uniform within the cup base.

In a 30th embodiment of the invention, it is provided that the permanent magnet of the at least one oscillation sensor has at least two slits, for example also a plurality thereof and/or extending essentially parallel to one another and/or essentially uniform.

In a 31st embodiment of the invention, it is provided that the at least one oscillation exciter is fed, at least at times during operation, by an electric, driving signal effecting oscillations of the measuring tube, for example bending oscillations of the measuring tube in an imaginary, primary plane of oscillation.

In a 32nd embodiment of the invention, it is provided that the first oscillation sensor and the at least one oscillation exciter are embodied with essentially the same construction.

In a 33rd embodiment of the invention, it is provided that the at least one oscillation exciter includes at least one coil, for example a coil mechanically connected, especially rigidly coupled, with the counteroscillator. Developing this embodiment of the invention further, it is additionally provided that the at least one oscillation exciter further includes, magnetically coupled with the coil, a permanent magnet, which is placed within a magnet cup composed at least partially of magnetically conductive material. The permanent magnet is secured to a cup base, for example a cup base secured to the measuring tube. For the purpose of further improvement of the accuracy of the measuring transducer, it is additionally provided that, in such case, a cup wall of the magnet cup extends, for example, essentially circular-cylindrically and/or tubularly, from the cup base of the at least one oscillation exciter, for example in the direction of the counteroscillator and/or in the direction of bending oscillations of the measuring tube relative to the counteroscillator, and has at least one slit, for example a slit extending at least sectionally in the direction of oscillations of the measuring tube relative to the counteroscillator.

In a 34th embodiment of the invention, it is provided that the first oscillation sensor is placed on the inlet side of the measuring tube. Developing this embodiment of the invention further, the measuring transducer additionally includes at least a second oscillation sensor, for example a second oscillation sensor of construction essentially equal to that of the first oscillation sensor and/or a second oscillation sensor placed on the outlet side of the measuring tube.

In a 35th embodiment of the invention, it is provided that the measuring tube is surrounded, at least partially, by the counteroscillator.

In a 36th embodiment of the invention, it is provided that the counteroscillator is essentially tubular.

In a 37th embodiment of the invention, it is provided that the counteroscillator is essentially straight.

In a 38th embodiment of the invention, it is provided that the measuring tube is essentially straight. Developing this embodiment of the invention further, it is additionally provided that also the counteroscillator is essentially tubular and essentially straight. In this way, it is additionally also possible to orient measuring tube and counteroscillator essentially coaxially with one another and/or also to allow the counteroscillator to execute, at least at times during operation, bending oscillations about the bending oscillation axis, especially bending oscillations essentially coplanarly with the bending oscillations of the measuring tube. Moreover, the measuring tube can, consequently, execute during operation, for example for the purpose of viscosity measurement, torsional oscillations about a torsional oscillation axis essentially parallel, especially coincident, with the bending oscillation axis.

In a 39th embodiment of the invention, it is provided that the measuring tube extends with an essentially constant, especially circular, ring-shaped, cross section between the two coupling zones.

In a 40th embodiment of the invention, it is provided that the measuring tube has an essentially cylindrical shape, especially a circular-cylindrical shape.

In a 41st embodiment of the invention, the measuring transducer further includes a transducer housing, which houses an inner part of the measuring transducer formed by means of measuring tube, counteroscillator, oscillation exciter and the at least one oscillation sensor.

In a 42nd embodiment of the invention, it is provided that the measuring tube communicates with the pipeline via an inlet-side-opening, inlet tube piece and an outlet-side-opening, outlet tube piece. Developing this embodiment of the invention further, the measuring transducer additionally includes a transducer housing affixed to the inlet tube piece and to the outlet tube piece.

The invention is based, among other things, on the surprising discovery that, on the one hand, predominantly constant parts of magnetic fields acting externally on measuring transducers of the type being discussed have, in the sense of the desired accuracy of measurement, a significant influence on the zero point, while, however, on the other hand, less the movement of the coils in the magnetic field lead, as such, to corresponding disturbances in the measuring signals delivered by the oscillation sensors, but instead, rather, the periodic variation of the relative separation between vibrating measuring tube and counteroscillator. This, in turn, especially, may cause, due to the periodic variation of the relative separation, in the end, the magnetic resistance of the inner part, and consequently, the spatial distribution of the magnetic field within the measuring transducer as a whole, and, along with that, also the magnetic field density to vary repetitively in the region of the oscillation sensors, in sequence with the oscillation frequencies of the wanted mode. As a result of the change with respect to time of the magnetic field density in the region of the oscillation sensors, thus, corresponding voltages can be induced in the coil as well as also in the connected lines, while, on the other hand, however, also corresponding eddy currents can form in large-area, metal parts, which themselves can lead, in turn, to voltage induction in the oscillation sensor. As especially pre-destined for disturbances of the described kind is, in such case, the magnet cup usually employed in the case of such oscillation sensors.

A basic idea of the invention is effectively to lessen, in simple manner, by means of slits, disturbances of the zero point produced via the earth's magnetic field in the measuring transducer, or as a result of the periodic changes of its field density in the region of the oscillation sensors, by suitably modifying the magnetic cup identified as especially neuralgic in the sense of a stable zero point, while keeping, as largely as possible, the already established form of construction and materials in measuring transducers of the type been discussed, as well as their otherwise good characteristics as regards the conducting and homogenizing of the magnetic field of the permanent magnet effecting the actual measuring effect within the oscillation sensor.

Apart from the fact that the influence of the magnetic field is less, the more slits are provided in the magnet cup, it has surprisingly been found that already the use of oscillation sensors with, in each case, a single slit running along the cup wall yields a significant improving of the zero-point stability of the measuring transducer. Conversely, the number and/or the size of the slits finally actually provided in the magnet cup has a limit, at least to the extent that, thereby, vibration resistance and stiffness of the magnet cup is reduced and then a tendency for undesired eigenvibrations of the magnet cup arise. Equally, it is wise to limit the number of the slits to as small a number as possible, toward the goal of achieving sufficient homogenizing and guiding of the magnet field of the permanent magnet suitable for the actual measurement. A weighing of the costs and benefits will lead, in practice, more to a choosing of about two to four slits per oscillation sensor as adequate for delivering the usually desired accuracies of measurement, as well as also, in the sense of lowest possible manufacturing costs, results which are quite satisfactory.

BRIEF DESCRIPTION OF THE DRAWINGS

The invention and advantageous embodiments thereof will now be explained on the basis of an example as illustrated in the figures of the drawing; equal parts are provided with equal reference characters in the figures. In case supportive of clarity, already mentioned reference characters are not repeated in subsequent figures. The figures show as follows:

FIG. 3 the measuring transducer of FIG. 2 sectioned in a side view;

FIG. 4 the measuring transducer of FIG. 2 in a first cross section;

FIG. 5 the measuring transducer of FIG. 2 in a second cross section;

DETAILED DESCRIPTION OF EXEMPLARY EMBODIMENTS

Figure 1:
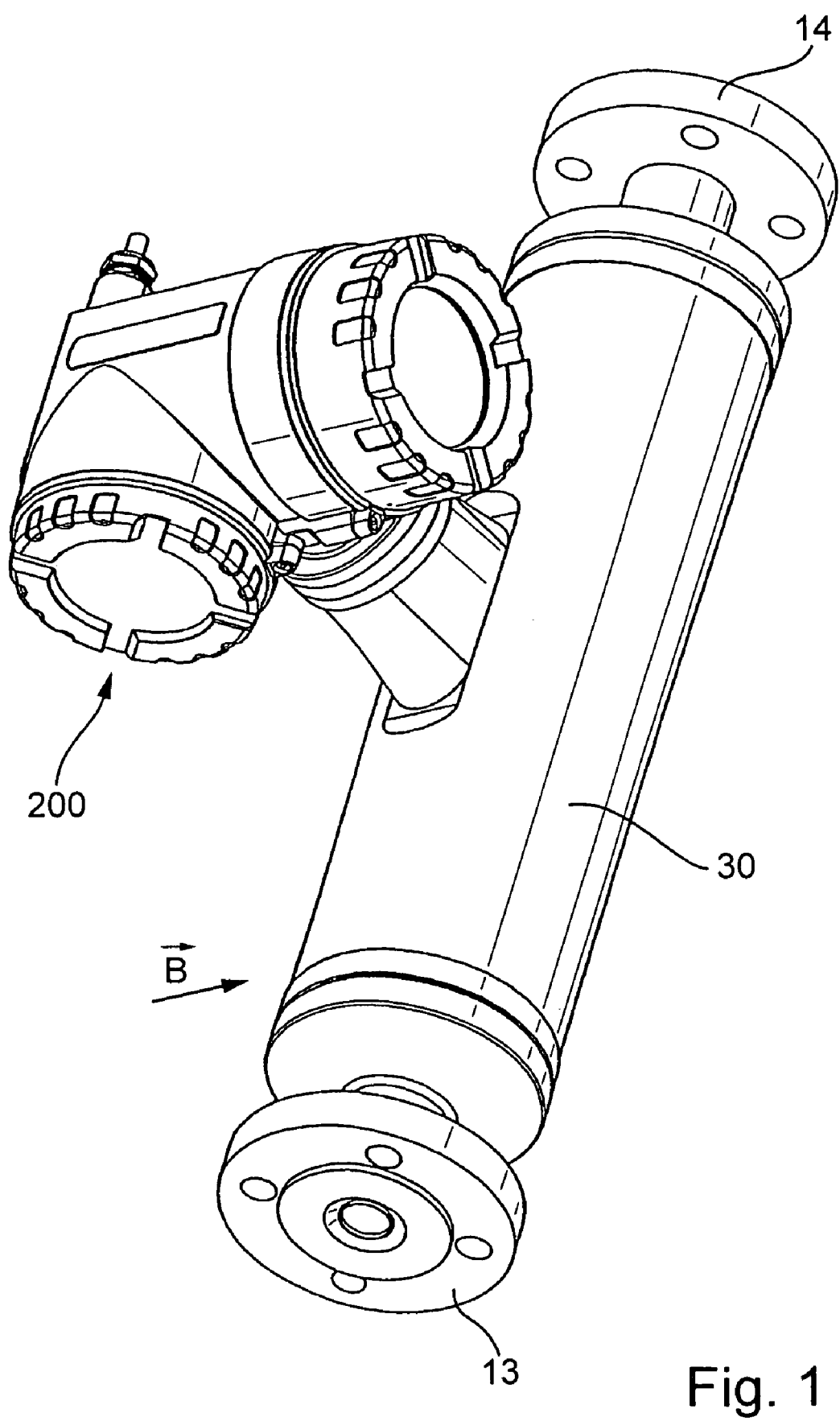
FIG. 1 an in-line measuring device joinable into a pipeline for measuring at least one parameter of a medium conveyed in the pipeline.

While the invention is susceptible to various modifications and alternative forms, exemplary embodiments thereof have been shown by way of example in the drawings and will herein be described in detail. It should be understood, however, that there is no intent to limit the invention to the particular forms disclosed, but on the contrary, the intention is to cover all modifications, equivalents, and alternatives falling within the spirit and scope of the invention as defined by the intended claims.

FIG. 1 shows an in-line measuring device, which can be joined into a pipeline (not shown). The measuring device can be, for example, an in-line measuring device embodied as a Coriolis mass flow measuring device, density measuring device, viscosity measuring device, or the like, which serves for measuring and/or monitoring at least one parameter, for example a mass flow, e.g. mass flow rate, a density, a viscosity, etc. of medium flowing in the pipeline. The inline measuring device includes for such purpose a measuring transducer of vibration-type, electrically connected to an operating and evaluating electronics (not shown) accommodated in a corresponding electronics housing 200. During operation, medium to be measured flows through the measuring transducer.

FIGS. 2 to 5 use an example of an embodiment to show, schematically in different sectional views, the principal construction of such a measuring transducer of vibration-type. Additionally, the principal mechanical structure of the measuring transducer as well as the manner of action of such structure, as shown by a way of example, are comparable with those of the measuring transducers shown in US-A 2007/0119265, US-A 2007/0119264, U.S. Pat. No. 6,691,583, U.S. Pat. No. 6,840,109.

The measuring transducer serves for producing mechanical, reaction forces in a medium flowing therethrough, e.g. mass-flow-dependent, Coriolis forces, density-dependent, inertial forces and/or viscosity-dependent, frictional forces, which measurably, especially as registerable by sensor, react on the measuring transducer. Derived from these reaction forces, e.g. a mass flow m, a density $\rho$ and/or a viscosity $\eta$ can then be measured in manner known to those skilled in the art. For conveying the medium, the measuring transducer includes at least one measuring tube 10 (in the example of an embodiment shown here, a single, essentially straight, measuring tube 10), which, in operation, is caused to vibrate, for example in a natural, bending oscillation mode and/or in a natural, torsional oscillation mode, such that it is repeatedly elastically deformed to oscillate about a static rest position. In such case, the measuring transducer has at least a first natural mode of oscillation, in which at least the measuring tube can execute bending oscillations in an imaginary, primary plane of oscillation XZ.

For minimizing disturbing influences acting on the measuring tube 10 as well as also for reducing oscillatory energy given off by the measuring transducer to the connected pipeline, provided additionally in the measuring transducer is a counteroscillator 20 (here extending essentially straight and essentially parallel to the measuring tube 10). This is, as also shown in FIG. 2, affixed to the measuring tube, associated with the formation, on the inlet side, of a first coupling zone 11# essentially defining an inlet end of the measuring tube 10 and associated with the formation, on the outlet side, of a second coupling zone 12# essentially defining an outlet end of the measuring tube 10.

Counteroscillator 20 can be e.g. tubular or box-shaped and so connected on the inlet end and on the outlet end with the measuring tube 10 that it is, as quite usual in the case of such measuring transducers, essentially directed coaxially with the, here, essentially straight measuring tube 10 and such that the measuring tube 10 is, at least partially, surrounded by the counteroscillator 10. In an embodiment of the invention, the counteroscillator is additionally so matched to the measuring tube as regards mass regards mass and bending stiffness that, in comparison to the bending oscillations of the measuring tube, it executes quite appreciable bending oscillations of equal frequency and, thus, executes, at least at times during operation, bending oscillations about the bending oscillation axis. It can, however, also be of advantage, when the counteroscillator 20 is designed to be significantly heavier than the measuring tube 10, so that it has, in comparison with the measuring tube, at least nominally, a smaller eigenfrequency and, consequently, scarcely oscillates during operation or, at least in comparison with the measuring tube, does not execute oscillations worth mentioning.

For bringing medium to be measured into, and draining such medium away from, the measuring tube 10, such is connected, via an inlet tube piece 11 opening on the inlet side in the region of the first coupling zone and via an outlet tube piece 12, especially an outlet tube piece essentially identical to the inlet tube piece 11, opening on the outlet side in the region of the second coupling zone, to a pipeline (not shown) respectively supplying and draining the medium. Inlet tube piece 11 and outlet tube piece 12 are, in the illustrated example of an embodiment, essentially straight and aligned with the measuring tube 10, as well as with a longitudinal axis L essentially connecting the coupling zones. Advantageously, measuring tube 10 and inlet- and outlet-tube-pieces 11, 12 can be embodied as one piece, so that e.g. a single, tubular stock can serve for their manufacture. Instead of measuring tube 10, inlet tube piece 11 and outlet tube piece 12 being formed by segments of a single, one-piece tube, such can, in case required, however, also be manufactured by means of separate pieces of stock subsequently joined together, e.g. by welding. In an embodiment of the invention, the measuring tube is additionally so embodied that it extends with essentially constant cross section, especially circular cross section, between the two coupling zones. Especially, it is additionally provided that the measuring tube 10 is formed essentially cylindrically, especially circular-cylindrically.

Figure 2:
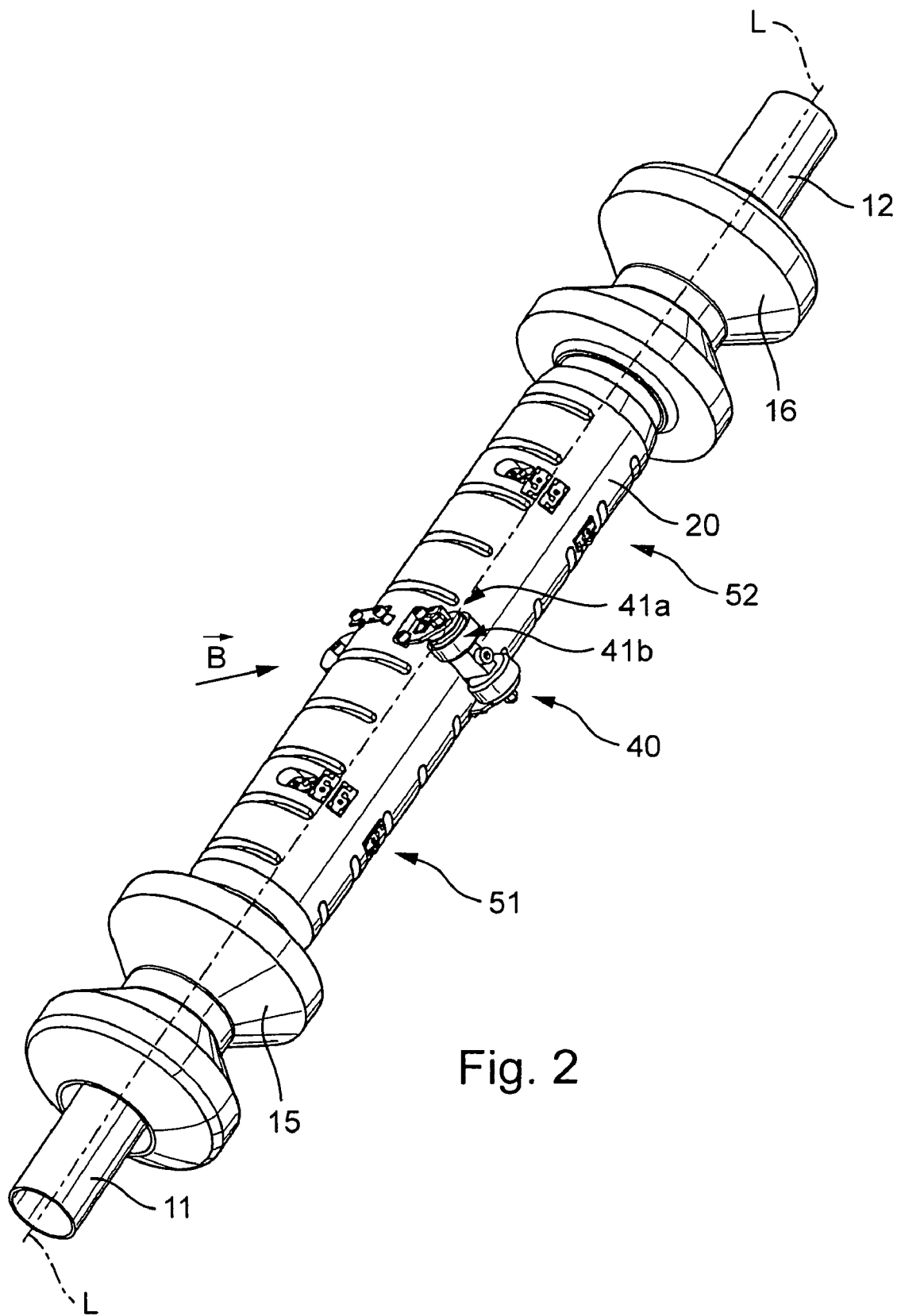
FIG. 2 in perspective, side view, an example of a measuring transducer of vibration-type suitable for the in-line measuring device of FIG. 1 and including a measuring tube and a counteroscillator, as well as terminal outliers.

The inner part of the measuring transducer formed by means of the measuring tube 10, the counteroscillator 20, the inlet tube piece 11 and the outlet tube piece 12 is, as evident from the combination of FIGS. 1 and 2, additionally held oscillatably in a transducer housing 30 surrounding such inner part, tightly to leakage of medium and also, within limits, pressure tightly. Transducer housing 30 is appropriately affixed on the respective ends of the in- and out-let tube pieces 11, 12 away from their respective coupling zones. For the case in which the measuring transducer is to be assembled with the pipeline releasably, first and second flanges 13, 14 are provided on the inlet tube piece 11 and the outlet tube piece 12, respectively. Flanges 13, 14 can, in such case, at the same time, be embodied as integral components of the transducer housing 30. In case necessary, the in- and out-let tube pieces 11, 12 can, however, also be connected directly with the pipeline, e.g. by means of welding or brazing.

For producing mechanical oscillations of the measuring tube 10, be they bending oscillations and/or torsional oscillations, the measuring transducer further includes an exciter mechanism 40, especially an electrodynamic exciter mechanism. This serves for converting an electrical exciter energy $E_{exc}$ fed by means of the operating and evaluating electronics in the form of a correspondingly conditioned, electric, driver signal, e.g. having a controlled current and/or a controlled voltage, into an exciter force $F_{exc}$ acting, e.g. in pulse form, clocked or harmonically, on the measuring tube 10 and elastically deforming such in the above-described manner. The exciter force $F_{exc}$ can, in such case, as shown schematically in FIG. 4, be embodied bi-directionally or, however, also unidirectionally and can be tuned in manner known to those skilled in the art as regards its amplitude e.g. by means of a current- and/or voltage-control circuit and, as regards its frequency, e.g. by means of a phase control loop. Especially, the exciter mechanism is, as quite usual in the case of such measuring transducers, further so embodied and arranged in the measuring transducer that it acts measuring transducer that it acts on the measuring tube essentially centrally and/or is affixed thereto externally at least pointwise along an imaginary, central, peripheral line of the measuring tube. The exciter mechanism 40 can be e.g. a simple electrodynamic plunger-coil arrangement acting differentially on the measuring tube 10 and counteroscillator 20 and including at least one cylindrical exciter coil 41a secured directly, or, as shown in FIGS. 2 and 4, mediately, to the counteroscillator 20. During operation, an electrical, exciter current, or an exciter current portion branched therefrom flows through the exciter coil. Additionally, the plunger-coil arrangement includes a permanently magnetic armature 41b extending at least partially into the exciter coil and affixed externally, especially centrally, on the measuring tube 10. In the example of an embodiment shown here, the at least one exciter coil 41a of the exciter mechanism 40 is affixed to a lever 41', here a lever connected with the measuring tube 10, and acts via such and in interaction with the permanently magnetic armature 41b, here affixed externally to the counteroscillator 20, on measuring tube 10 and counteroscillator 20. The exciter mechanism 40 shown in the example of an embodiment includes, moreover, three additional plunger-coil arrangements 42, 43, 44 of the aforementioned kind, in each case acting differentially on measuring tube 10 and counteroscillator 20. Alternatively to the aforementioned, electrodynamic, plunger-coil arrangements, the exciter mechanism 40 can, however, also be implemented e.g. as electromagnets or also as seismic exciters. Also, in the case of measuring transducers of the aforementioned kind, it is additionally also possible to secure the coils and/or the armatures, for example, directly to the measuring tube or to the counteroscillator, without using an intermediating lever.

For registering oscillations at least of the measuring tube 10 relative to the counteroscillator 20, the measuring transducer further includes at least one oscillation sensor 51, especially an electrodynamic oscillation sensor and/or one differentially registering the relative oscillations of measuring tube and counteroscillator, for counteroscillator, for delivering at least at times during operation, an oscillation measurement signal $s_1$ representing vibrations of the measuring tube 10. The at least one oscillation sensor 51 includes, as quite usual in the case of such measuring transducers, a coil 51a, here affixed to the counteroscillator 20, as well as an armature 51b embodied in the form of a permanent magnet, magnetically coupled with the coil 51a and, here, secured to the measuring tube 10. In an embodiment of the invention, the permanent magnet is composed at least partially, especially predominantly or completely, of a rare earth alloy, such as, for instance, AlNiCo, NyFeB, SmCo or the like. Alternatively or in supplementation, the permanent magnet can, however, also be manufactured of a ferrite.

Sensor coil 51a is arranged as near as possible to the permanently magnetic armature 51b, here affixed to the counteroscillator 20, and so magnetically coupled therewith that there is induced in the sensor coil 51a a variable measurement voltage, which is influenced by lateral relative movements between measuring tube 10 and counteroscillator 20 changing a relative separation between sensor coil and armature and/or by relative rotational movements between measuring tube 10 and counteroscillator 20 changing a relative position of the sensor coil with respect to the armature. In case necessary, sensor coil 51a can, for such purpose, however also be affixed to the counteroscillator 20, and, in corresponding manner, the armature 51b coupled therewith can be affixed to the measuring tube 10.

Figure 7A:
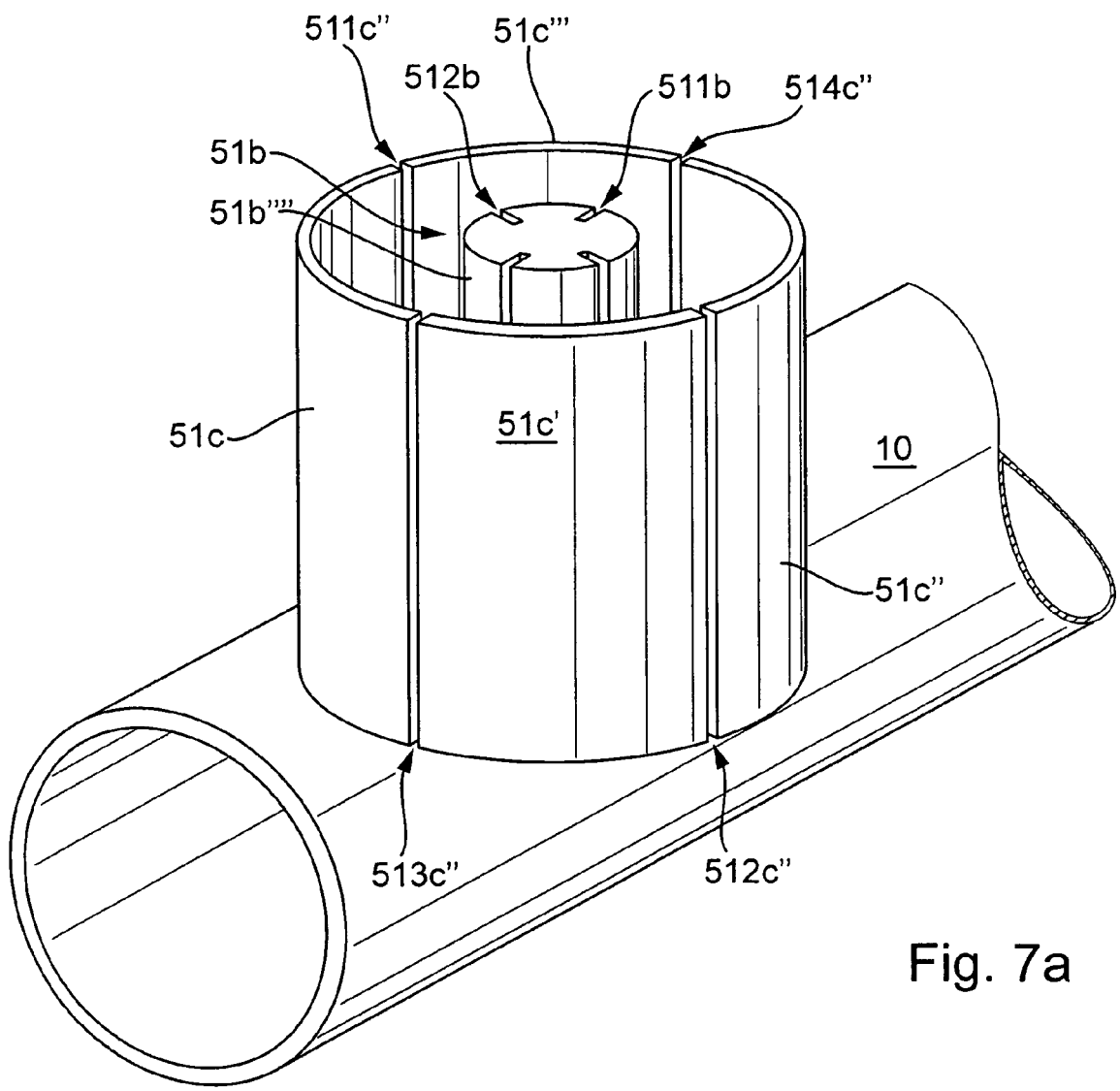
FIGS. 7a, b in different views, a magnet cup of an oscillation sensor for a measuring transducer of FIG. 2.
Figure 7B:
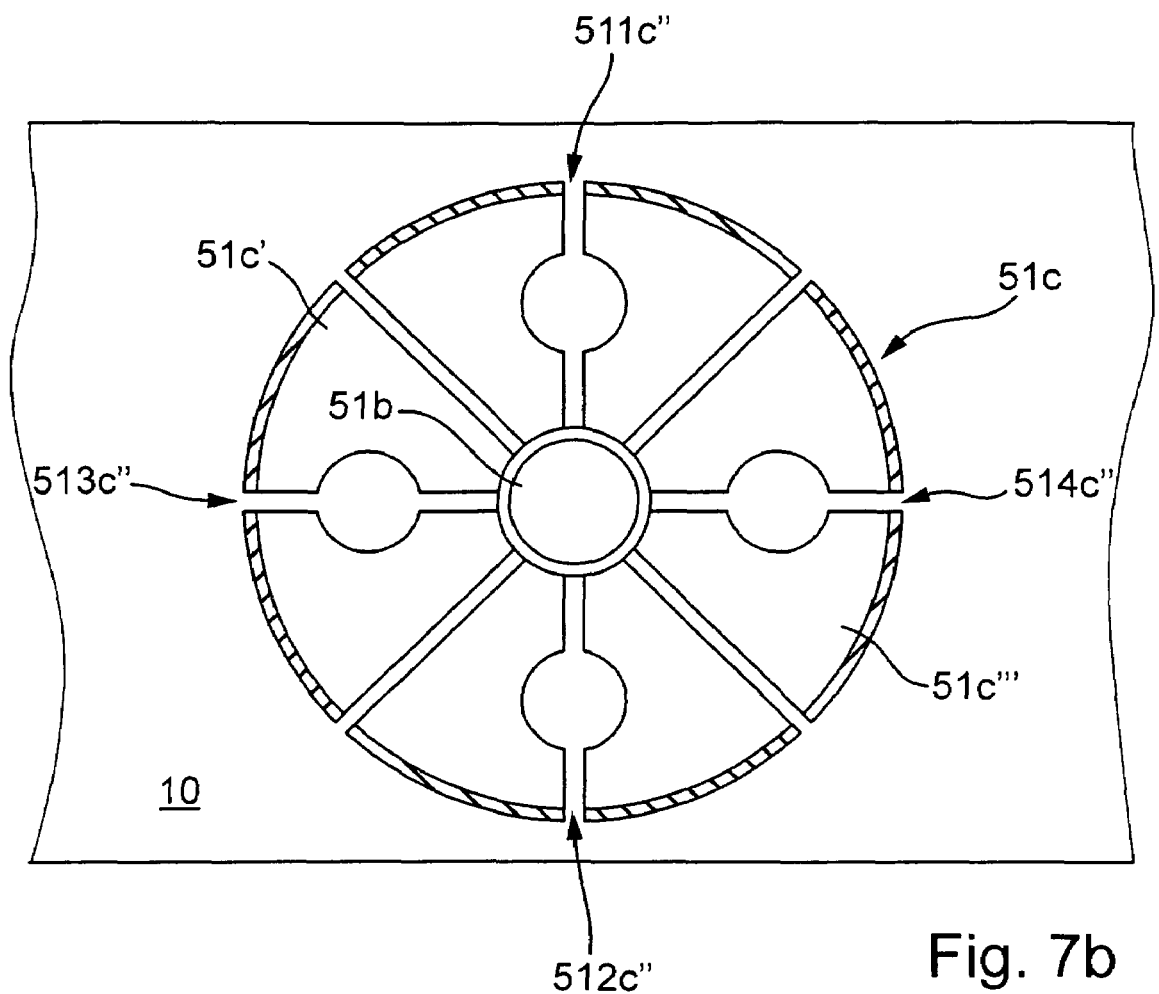

The permanent magnet 51b, especially a permanent magnet of elongated and/or rod shape, is, in turn, as shown schematically in FIGS. 7a and 7b, placed within a magnet cup 51c composed at least partially of a magnetically conductive material and is secured to a cup base 51c', for example a cup base secured directly to the measuring tube 10. In such case, it can be quite advantageous to affix the permanent magnet 51b to the cup base 51c' essentially in a center thereof. In a further embodiment of the invention, the magnet cup 51c is composed, additionally, at least partially, at least partially, especially predominantly or completely, of steel, such as for instance, a free-machining steel or a structural steel. Alternatively or in supplementation, the magnet cup 51c can, however, also be manufactured e.g. of a ferrite. Also extending from the cup base 51c' is a cup wall 51c'' of the magnet cup 51c, especially an essentially circular-cylindrical or tubular, cup wall. In a further development of the invention, permanent magnet 51b and coil 51a of the at least one oscillation sensor 51 are oriented essentially extending coaxially with one another. For the already indicated case, in which the cup wall 51c'' of the magnet cup 51c has an essentially circular-cylindrical and/or tubular form, it is provided in a further development of the invention, that permanent magnet 51b and cup wall 51c'' are oriented essentially coaxially extending with one another.

In a further development of the invention, the measuring transducer includes, besides the at least one oscillation sensor 51, as shown in FIG. 3, at least one additional oscillation sensor 52, which delivers, at least at times during operation, a corresponding, second oscillation signal $s_2$. For detecting inlet-side and outlet-side oscillations of the measuring tube 10, the first of the at least two oscillation sensors 51, 52 is, as shown schematically in FIG. 2 or 3, placed on the inlet-side of the measuring tube 10, while the second of the at least two oscillation sensors 51, 52 is arranged on the outlet-side of the measuring tube 10. The two oscillation sensors 51, 52, especially such oscillation sensors embodied to have essentially equal constructions relative to one another, are, in such case, advantageously arranged on one and the same side on the measuring tube 10 and on the counteroscillator 20, and are, in such case, so placed in the measuring transducer spaced from each of the two coupling zones 11#, 12#, that they have, in each case, essentially the same separation from the middle of the measuring tube 10 and/or from the, in each case, nearest of the two coupling zones 11#, 12#.

The exciter mechanism 40, as well as also the at least one oscillation sensor 51, are electrically connected with the mentioned operating- and evaluating-electronics of the in-line measuring device, furthermore, by means of connecting lines, which, in turn, are led, at least sectionally, inside the transducer housing; compare, in this connection, especially also the initially mentioned German Patent Applications 102006062220.0, 102006062219.7 and 102006062185.9 of the assignee. The connection lines can, in such case, be embodied, at least in part, as electrical line wires encased, at least sectionally, by an electrical insulation and can be e.g. in the form of "twisted-pair" lines, flat-band cables and/or coaxial cables. Alternatively or in supplementation, the connecting lines can be formed, at least sectionally, also by means of conductive traces of a circuit board, especially a flexible circuit board, which may, as required, be lacquer-coated.

In a further embodiment of the invention, measuring tube 10, counteroscillator 20, the at least one oscillation sensor 51, or the oscillation sensors, as the case may be, and the exciter mechanism 40, are so totally matched to one another as regards their mass distribution that the so-formed, inner part of the measuring transducer suspended by means of the inlet and outlet tube pieces 11, 12 has a center of mass CM, which lies at least within the measuring tube 10, preferably however as near as possible to the longitudinal axis L of the measuring tube. Additionally, the inner part is further so constructed that it has a first principal axis of inertia I1 aligned with the inlet tube piece 11 and the outlet tube piece 12 and lying at least sectionally within the measuring tube 10. As a result of the positioning of the center of mass CM of the inner part, especially however also due to the above-described position of the first principal axis of inertia I1, the torsional oscillations and the bending oscillations of the measuring tube 10 are, to a largest extent, mechanically decoupled from one another, at least in the wanted mode.

The inner part of the measuring transducer is, in a further embodiment of the invention, so constructed, that a first principal axis of inertia I1 thereof essentially coincides with the above-mentioned, longitudinal axis L. Additionally, in a further embodiment of the invention, the inner part of the measuring transducer is so constructed that a second principal axis of inertia I2 thereof essentially coincides with the above-mentioned, central axis.

Figure 6A:
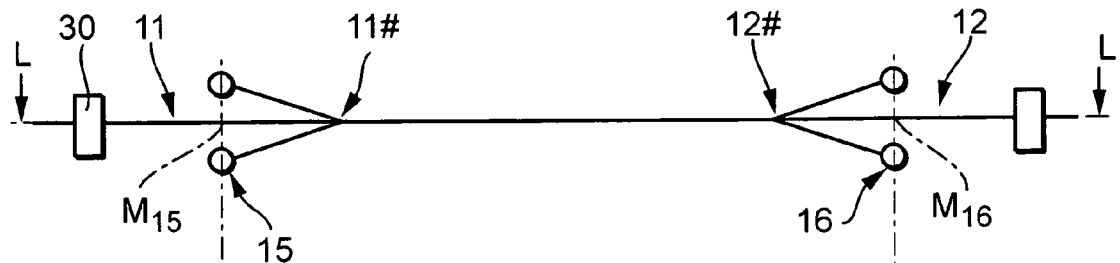
FIGS. 6a-d schematically, bending lines of the measuring tube and a counteroscillator oscillating in a lateral, bending oscillation mode.

For further improving accuracy of measurement and based on the measuring transducers proposed in the initially mentioned US-A 2007/0186685, US-A 2007/0119265, US-A 20070/119264, U.S. Pat. No. 6,691,583, or U.S. Pat. No. 6,840,109, the measuring transducer of the invention includes, in a further development of the invention, as also evident from the combination of FIGS. 2, 3 and 6a, additionally a first outlier 15 coupled with the inlet tube piece 11 and the measuring tube 10 in the region of the first coupling zone and having a center of mass $M_{15}$ lying in the region of the inlet tube piece 11, as well as a second outlier 16 coupled with the outlet tube piece 12 and the measuring tube 10 in the region of the second coupling zone and having a center of mass $M_{16}$ lying in the region of the outlet tube piece 12. In other words, the two outliers 15, 16, especially outliers of essentially equal construction, which may also be identical to one another, are so arranged in the measuring transducer that the respective centers of mass $M_{15}$, $M_{16}$ are spaced from the measuring tube 10. Especially, the centers of mass $M_{15}$, $M_{16}$ are aligned with the measuring tube 10. The two outliers 15, 16 are, thus, as a result, mounted eccentrically on the inlet and outlet tube pieces and, correspondingly, eccentrically also with respect to the measuring tube 10 and counteroscillator 20. The manner, in which the so-formed inner part acts, corresponds, in such case, to that of the inner parts shown in the mentioned us-a 2007/0186685, US-A 2007/0119265, US-A 20070/119264, U.S. Pat. No. 6,691,583, or U.S. Pat. No. 6,840,109. In order to enable as simple and cost-favorable manufacture of the outliers, as well as, finally, the measuring transducer, as possible, each of the two outliers 15, 16 can be embodied to be essentially tubular, or sleeve-shaped, so that essentially tubular, or sleeve-shaped, so that each can be formed essentially by means of a sleeve, especially a metal sleeve, which is pushed onto the counteroscillator 20, especially after the counteroscillator 20 has already been connected with the measuring tube 10. In a further development thereof, each of the sleeves, in such case, forming the respective outliers 15, 16 has at least one annular groove; compare, for this, also the mentioned US-A 2007/0186685, US-A 2007/0119265 or US-A 2007/0119264.

For manufacturing in- and out-let tube pieces, as well as the measuring tube, practically any material usual for such measuring transducers, such as e.g. stainless and/or austenitic steel, titanium, tantalum, zirconium, or, however, also nickel alloys, such as e.g. Hastelloy, can be used. For example, especially the application of titanium, tantalum, zirconium or also stainless steel, such as 316 L, 318 L, has proved as especially suitable for the measuring tube 10, as well as the inlet tube piece 11 and the outlet tube piece 12, while, for example, for reasons of cost savings, the application of cost-favorable and, most often, also magnetically favorably conducting, black steel is quite advantageous both for the counteroscillator 20 as well as for the possibly provided outliers 15, 16, as well as also for the transducer housing 30. Accordingly, the measuring tube 10 is additionally so embodied in a further development of the invention that it is composed at least partially, especially predominantly or completely, of a material, for example one of the aforementioned, usual measuring tube materials, which has a lower magnetic conductivity than a material of which the counteroscillator is, at least predominantly or also completely, composed. Especially, it is further provided that the counteroscillator 20 is composed at least partially, especially predominantly or completely, of a magnetically conductive material. Preferably the counteroscillator is, in such case, manufactured at least partially, especially predominantly or completely, of a magnetically conductive material, which has a relative permeability of at least 10, especially more than 100, such as a free-machining steel or a structural steel. Such steels are known to those skilled in the structural steel. Such steels are known to those skilled in the art, for example, also under the designations St37, St 38 or St 53.

During operation of the measuring transducer, measuring tube 10 is, as already mentioned in a number of instances above, so excited by means of the exciter mechanism 40, fed therefor during operation by an electric, driver signal, to execute, at least at times, lateral bending oscillations in the imaginary, primary plane of oscillation XZ, especially in the region of a natural resonance frequency of a corresponding, natural mode of oscillation, that it deflects in this so-called wanted mode at least partially, especially predominantly, according to a natural, first form of eigenoscillation. The bending oscillations in the wanted mode are, in such case, directed essentially transversely to a bending oscillation axis essentially parallel, especially coinciding, with the longitudinal axis L connecting the two coupling zones 11#, 12# imaginarily together. In an embodiment of the invention, in such case, it is further provided that the measuring tube is excited, at least at times during operation, by means of the exciter mechanism, in such a manner that it oscillates predominantly or exclusively in the imaginary, primary plane of oscillation.

Figure 6B:
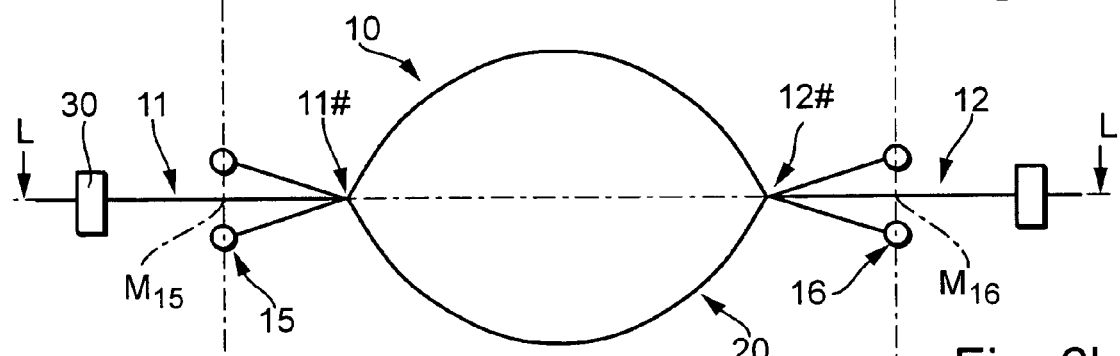
Figure 6C:
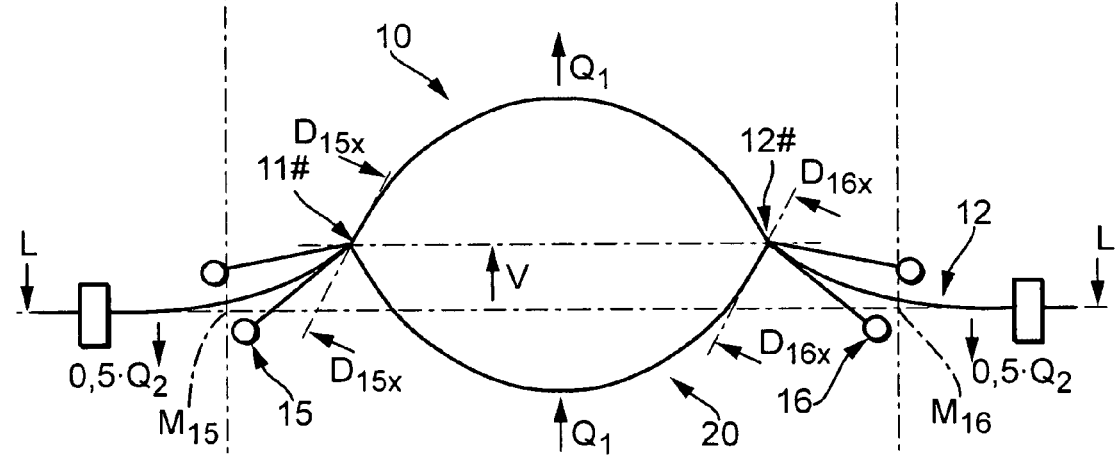
Figure 6D:
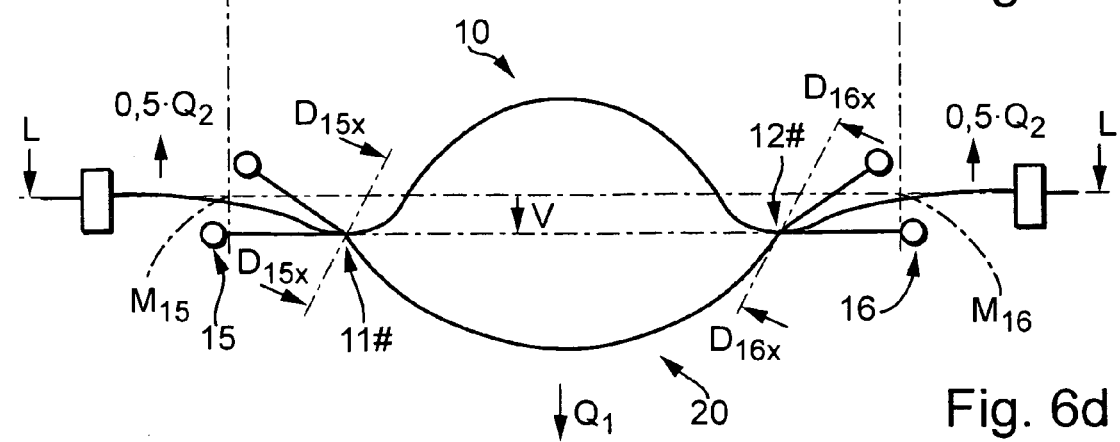

In a further embodiment of the invention, measuring tube 10 is, in such case, excited by means of an appropriately fed, exciter mechanism 40 to an oscillation frequency, $f_{exc}$, corresponding as exactly as possible to a natural resonance frequency of the so-called f1-eigenmode of the measuring tube 10, thus a symmetric eigenmode at which, as illustrated schematically in FIGS. 6b to 6d, the vibrating measuring tube 10, through which medium is not flowing, is bent out essentially symmetrically with respect to a central axis perpendicular to the longitudinal axis L and, in such case, exhibits essentially a single oscillation antinode; compare, in such respect, for example, also the initially mentioned US-A 2007/0119265, US-A 2007/0119264, or U.S. Pat. No. 6,840,109. In the same way, also counteroscillator 20 is, as shown schematically in FIG. 6b, likewise excited to execute bending oscillations during operation of the measuring operation of the measuring transducer; its bending oscillations are essentially coplanar with, but essentially opposite in phase to, the bending oscillations of measuring tube 10. In this way, measuring tube 10 and counteroscillator 20 thus oscillate during operation, at least at times and partially, laterally in a wanted mode, in which they execute jointly, essentially coplanar bending oscillations in the imaginary, primary plane of oscillation XZ.

For the case in which medium is flowing in the pipeline and, consequently, mass flow m is different from zero, Coriolis forces are induced in the through-flowing medium by means of the measuring tube 10 vibrating in the aforementioned manner. These, in turn, react on the measuring tube 10 and so effect an additional, sensorially registerable deformation (not shown) of the measuring tube 10 according to a natural, second form of eigenoscillation, which is essentially coplanarly superimposed on the excited, wanted mode. As a result, the measuring tube also oscillates in the Coriolis mode essentially in the imaginary, primary plane of oscillation XZ. The instantaneous character of the deformation of measuring tube 10 is, in such case, especially as regards its amplitude, also dependent on the instantaneous mass flow m. Serving as second form of eigenoscillation, the so-called Coriolis mode can be, as usual in the case of this type of measuring transducer, e.g. the form of eigenoscillation referred to as the anti-symmetric f2-eigenmode, thus that having two oscillation antinodes, and/or the form of eigenoscillation referred to as the anti-symmetric f4-eigenmode with four oscillation antinodes. In an embodiment of the invention, additionally, measuring tube 10 and counteroscillator 20 are so dimensioned that the empty measuring tube 10 has a lowest, natural eigenfrequency, $f_{10}$, which is greater than, or about equal to, a lowest natural eigenfrequency, $f_{20}$, of the counteroscillator 20. Especially, measuring tube 10 and counteroscillator 20 are, in such case, so dimensioned that the measuring tube 10 filled with water has a lowest natural eigenfrequency, $f_{10,H2O}$, which is at least equal to a lowest natural eigenfrequency, $f_{20}$, of the counteroscillator 20. In a further embodiment of the invention, it is additionally provided that measuring tube 10 and counteroscillator 20 are so matched with respect to one another as regards their oscillatory properties that a lowest natural eigenfrequency, $f_{10,H2O}$, of the measuring tube 10 then corresponds to at least 1.1 times a lowest natural eigenfrequency, $f_{20}$, of the counteroscillator 20, when the measuring tube is completely filled with water. In the case of a measuring tube of titanium having a nominal diameter DN of about 55 mm, a length, $L_{10}$, of about 570 mm and a wall thickness of about 2.5 mm, a natural resonance frequency, $f_{10,air}$, of the f1-eigenmode of the empty measuring tube would lie at about 550 Hz, while a natural resonance frequency, $f_{10,H2O}$, of the f1-eigenmode of the measuring tube filled with water would amount to about 450 Hz.

In a further development of the invention, especially also based on the measuring transducer disclosed in U.S. Pat. No. 6,840,109, the measuring tube 10 further executes, during operation, at least at times, especially simultaneously with the aforementioned bending oscillations, torsional oscillations about a torsional oscillation axis essentially parallel with the longitudinal axis L, or with the aforementioned bending oscillation axis, as the case may be. Torsional oscillation axis, bending oscillation axis, as well as also the longitudinal axis L can, as quite usual in the case of such measuring transducers, be essentially coincident. For the above-described measuring tube 10, for example, a lowest natural resonance frequency for the torsional oscillations would be in the region of about 750 Hz.

As already mentioned, in the case of measuring transducers of the aforementioned kind, especially in the case of those having a non-magnetic measuring tube and, in comparison therewith, a counteroscillator which can, quite certainly, be magnetic, a special problem is that the equally magnetic armature and/or magnet cup varies the field density, with respect to time, of magnetic fields B, such as, for instance, the earth's magnetic field, possibly coupled from the outside into the measuring transducer and traversing such in the region of the oscillation sensors, whereby disturbing disturbing voltages can be induced and superimposed on the actual oscillation measurement signal. For reducing such disturbances, it is, therefore, further provided that, in the measuring transducer of the invention, at least one slit 511c" is formed in the cup wall 51c", for example a cup wall 51c" having a circular-cylindrical and/or tubular form, extending from the cup base 51c', essentially in the direction of the coplanar oscillations of measuring tube 10 and counteroscillator 20.

In a further embodiment of the invention, the at least one slit 511c" has, at least sectionally, especially predominantly or completely, an essentially straight form and/or is so formed that it extends within the cup wall 51c" at least sectionally essentially in the direction of lateral, e.g. also coplanar, bending oscillations of measuring tube 10 and counteroscillator 20, thus extending, especially, in the imaginary, primary plane of oscillation XZ. Alternatively thereto or in supplementation thereof, the at least one slit 511c" can extend within the cup wall 51c", however, also, at least sectionally, inclined and/or helically. Without regard to the actual shape and/or length of the at least one slit 511c" within the cup wall 51c", a basic consideration is that it is, on the whole, of advantage to make the slit as narrow as possible, in order to maintain the stiffness of the magnet cup. This is the more-so true, since the width of the slit 511c" actually has only a small influence on the desired effectiveness of the disturbance suppression. Taking this into consideration, in a further embodiment of the invention, the at least one slit 511c" is so formed that it has a greatest width which is less than 1 mm.

In a further embodiment of the invention, permanent magnet 51b and the at least one slit 511c" extending within the cup wall are so formed and oriented relative to one another that both extend, at least sectionally, especially predominantly or entirely, essentially parallel to one another.

In another embodiment of the invention, the at least one slit 511c" extending within the the cup wall 51c" is so formed that it extends up to a free edge 51c''' of the magnet cup 51c, with, here, the free edge 51c''' essentially facing toward the counteroscillator 20. In this case, it can, additionally, be of special advantage to form the at least one slit 511c, additionally, such that it extends, starting from said edge of the magnet cup 51c, along the cup wall 51c", at least until the cup base 51c'.

Alternatively to, or in supplementation of, the aforementioned embodiments, it is provided in a further embodiment of the invention, that, as shown in FIG. 7b, also the cup base 51c' is slit. Especially, in such case, the at least one slit 511c" extending within the cup wall is lengthened in such a manner that it extends, on occasion, at least sectionally, also along the cup base 51c', for example as shown schematically in FIG. 7b, in the direction of a radius of the cup base 51c". Additionally, the effect of the at least one slit formed in the cup base can be further improved by, as shown schematically in FIG. 7b, sectionally widening it, for example, in the form of a corresponding bore in the cup base.

Although, already, a significant improvement of the zero-point stability of the pertinent measuring transducer can be achieved, in each case, by means of a single slit extending along the cup base 51c", it was possible, as already mentioned, to determine that the influence of externally in-coupled magnetic fields B disturbing the measurement becomes, as a whole, less, the greater the number of slits provided in the magnet cup. In a further development of the invention, for additional improvement of disturbance suppression, it is, therefore, further provided that the magnet cup has not only a single slit, but, instead, as also shown schematically in FIGS. 7a and 7b, at least two or more of such slits 511c", 512c", 513c", 514c", which, for example, lie essentially parallel and/or essentially uniformly, at least within the cup wall. As explained above using the example of one slit, also in the case of a plurality of slits in the magnet cup 51c of the oscillation sensor 51, two or more such slits can be formed slits can be formed in the cup base 51c', for example, in turn, essentially radially extending, and/or formed essentially uniformly. It is, however, to be noted here, that the number of the applied slits should be limited sensibly, in turn, at least as regards before and after, having sufficient homogenizing and suitable guidance of the magnet field of the permanent magnet required for the actual oscillation measurement. For increasing the fatigue resistance and stiffness of the singly or multiply slit, magnet cup and thus, associated therewith, for preventing undesired eigenvibrations of the same, it can, moreover, be of advantage to embed the magnet cup or at least slit sections thereof, completely or partially in electrically non-conductive ceramic and/or electrically non-conductive, synthetic material, such as e.g. an epoxide resin and/or at least partially fill the slits therewith.

Alternatively to or in supplementation of the aforementioned multiple slitting of the magnet cup, a further improvement of the disturbance suppression can also be achieved by, as also indicated in FIG. 7a, at least sectionally slitting not only the magnet cup 51c, but also the permanent magnet 51b. In a further embodiment of the invention, in addition to the magnet cup, also the permanent magnet 51b has at least one slit 511b extending at least sectionally in the direction of the essentially coplanar oscillations of measuring tube 10 and counteroscillator 20. This slit 511b can, for example, be so embodied that it extends to a free end, or edge, 51b'''' of the permanent magnet 51b not connected with the measuring tube 10. Alternatively thereto or in supplementation thereof, the permanent magnet 51b can, furthermore, also have at least two, especially more, slits 511b, 512b, which may extend essentially parallel to one another and/or may be essentially uniform.

Figure 8A:
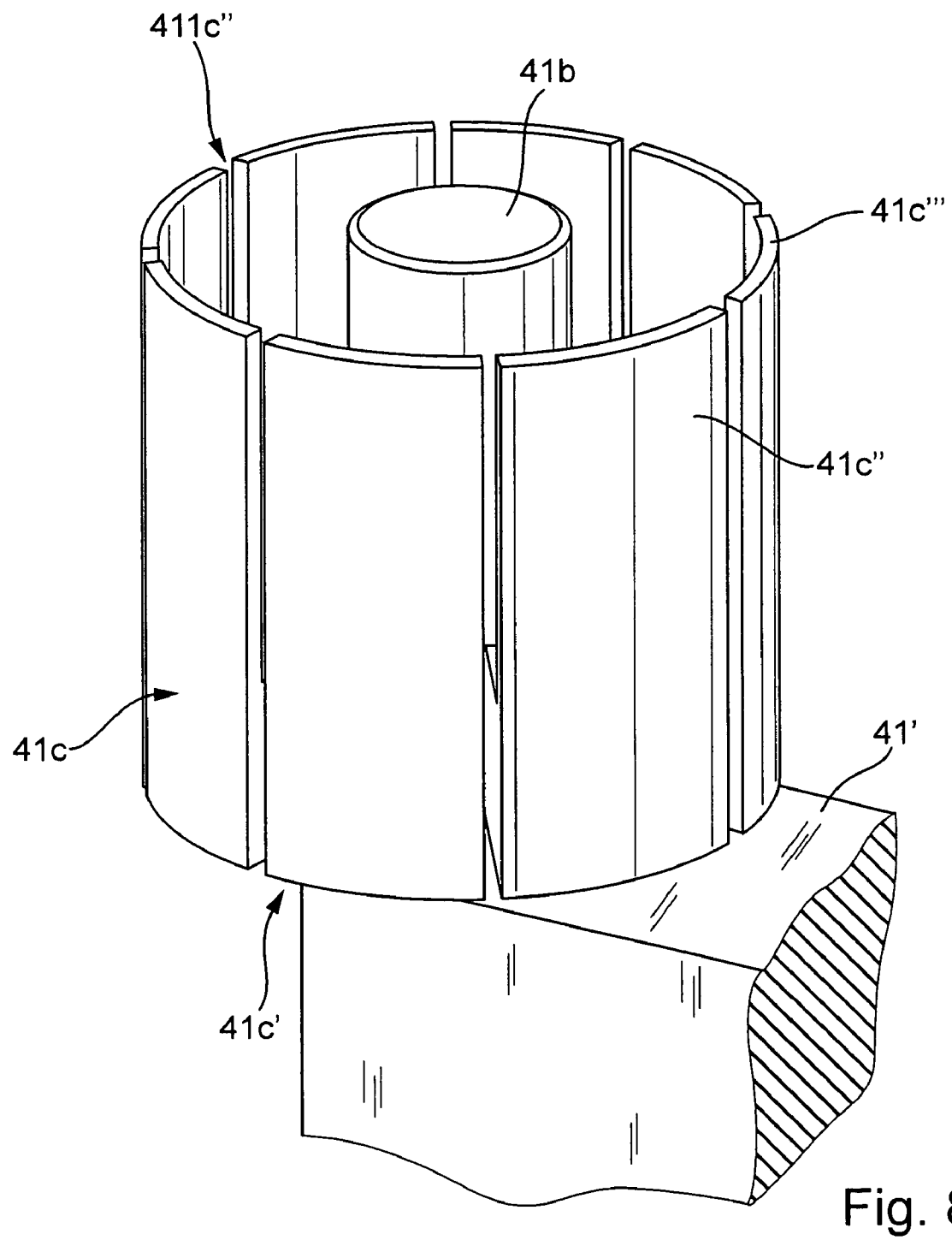
FIGS. 8a, b in different views, a magnet cup of an oscillation exciter for a measuring transducer of FIG. 2.
Figure 8B:
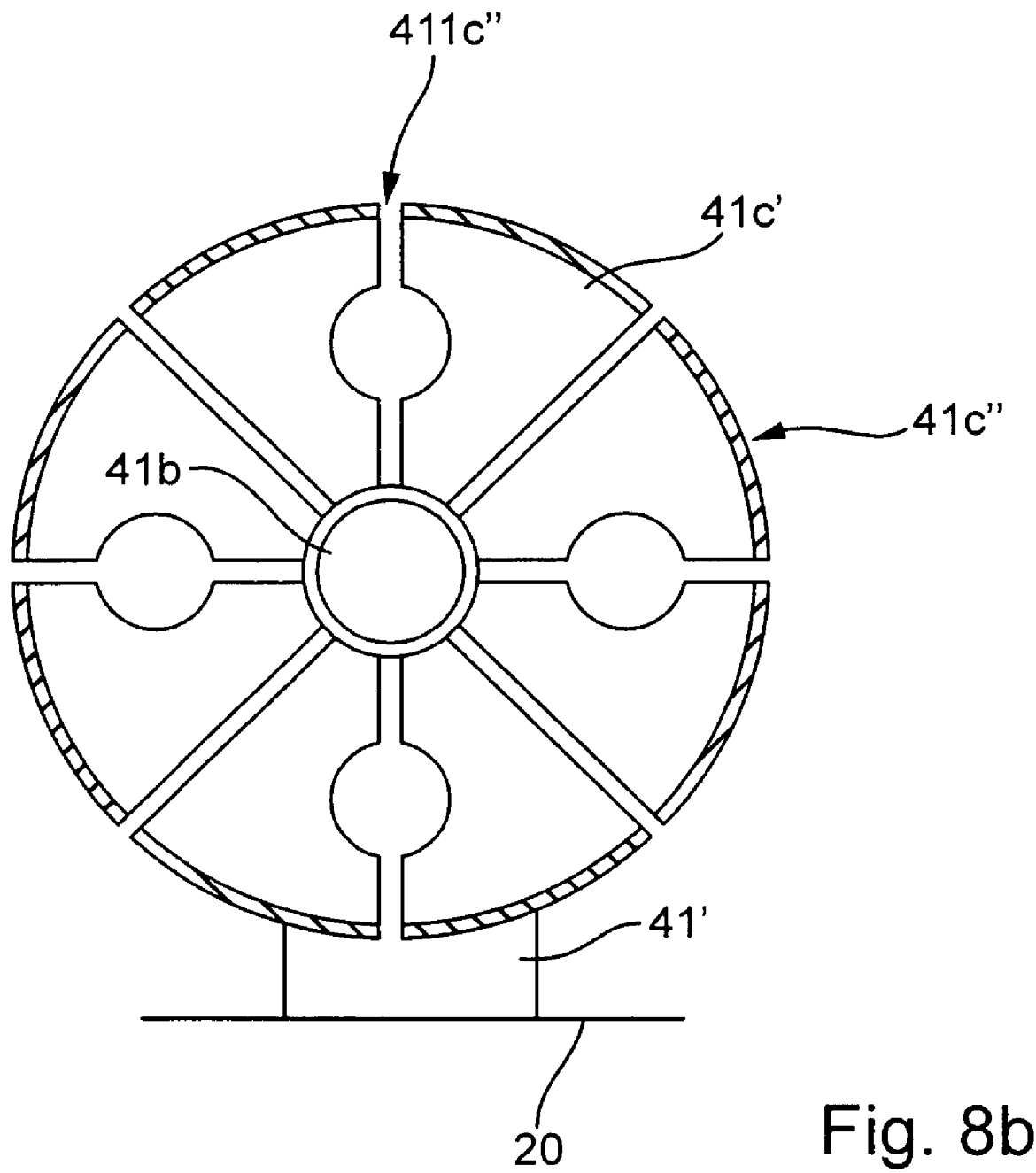

In a further development of the invention, it is additionally provided that the at least one oscillation exciter 41 and the at least one oscillation sensor 51 are built according to the same principle of action and especially are embodied with essentially the same construction. Accordingly, in a further embodiment of the invention, additionally also invention, additionally also the at least one oscillation exciter 41 has, furthermore, a magnet cup 41c, which is composed at least partially of magnetically conductive material, and includes, secured, for example, to the measuring tube 10 or, as clearly evident from the combination of FIGS. 4, 8a and 8b, to the counteroscillator 20, a cup base 41c', to which is held the permanent magnet 41b magnetically coupled with the coil 41a. Alternatively thereto, it is, however, also possible, as already mentioned, to affix the coil 41a to the counteroscillator 20 and the magnet cup 41c, with the permanent magnet 41b placed therein, accordingly to the measuring tube, so that then, thus, the at least one coil 41a of the exciter mechanism 40 is mechanically connected, especially rigidly, with the counteroscillator 20. In a further embodiment of the invention, it is additionally provided that also a cup wall 41c'' of the magnet cup 41c, especially one embodied essentially circular-cylindrically and/or tubularly, extending from the cup base 41c' of the magnet cup 41c of the at least one oscillation exciter 41, in the direction of the counteroscillator, or in the direction of the measuring tube, has at least one slit 411c'' extending, especially at least sectionally, in the direction of the oscillations of measuring tube 10 and counteroscillator 20 and/or to a free edge 41c''' of the magnet cup 41c.

As also recognizable without difficulty from the above explanations, the measuring transducer of the invention is distinguished by, among other things, the fact that, in comparison to conventional measuring transducers of the type discussed, from a design, or manufacturing, point of view, only small, easily implementable modifications of the oscillation sensor, or of the magnet cups conventionally already used therefor, are required in order to keep oscillation measurement signals of the above-described kind free, in very effective manner, of the disturbances induced as a result of external magnetic fields B, and especially also while keeping otherwise conventional construction of the measuring transducer and/or conventional wiring.

While the invention has been illustrated and described in detail in the drawings and forgoing description, such illustration and description is to be considered as exemplary not restrictive in character, it being understood that only exemplary embodiments have been shown and described and that all changes and modifications that come within the spirit and scope of the invention as described herein are desired to protected.

What is claimed is:

1. Measuring transducer of vibration-type for a medium flowing in a pipeline, said measuring transducer comprising:
    a measuring tube vibrating, at least at times, and serving for conveying medium to be measured;
    a counteroscillator affixed on an inlet-side to the measuring tube, to form a first coupling zone, and on an outlet-side to the measuring tube, to form a second coupling zone;
    an oscillation exciter for producing mechanical oscillations at least of the measuring tube relative to the counteroscillator; and
    a first oscillation sensor for registering oscillations at least of the measuring tube relative to the counteroscillator, said first oscillation sensor including a coil, a magnet cup composed at least partially of magnetically conductive material, and a permanent magnet placed within said magnet cup and magnetically coupled with the coil;
    wherein:
    the magnet cup includes a cup base and a cup wall extending from said cup base and said magnet cup being, and the cup wall of the magnet cup shows at least one slit.

2. Measuring transducer as claimed in claim 1, wherein the coil of the first oscillation sensor is affixed to the counteroscillator.

3. Measuring transducer as claimed in claim 1, wherein the permanent magnet of the first oscillation sensor is mechanically coupled with the measuring tube.

4. Measuring transducer as claimed in claim 1,
    wherein the cup base of the magnet cup is secured to the measuring tube; and/or
    wherein the cup wall is essentially circular-cylindrical and/or tubular; and/or
    wherein the cup wall extends from said cup base in the direction of the counteroscillator; and/or
    wherein the permanent magnet is held to the cup base of said magnet cup.

5. Measuring transducer as claimed in claim 1,
    wherein the permanent magnet, especially an elongated and/or rod-shaped permanent magnet, and the coil of the first oscillation sensor are oriented extending essentially coaxially relative to one another; and/or
    wherein permanent magnet and cup wall are oriented extending essentially coaxially relative to one another; and/or
    wherein the permanent magnet of the first oscillation sensor is affixed to the cup base essentially in a center thereof; and/or
    wherein also the permanent magnet of the first oscillation sensor is at least sectionally slit.

6. Measuring transducer as claimed in claim 1,
    wherein the permanent magnet of the first oscillation sensor and the at least one slit are oriented, at least sectionally, especially predominantly or entirely, extending essentially parallel to one another; and/or
    wherein the at least one slit is, at least sectionally, especially predominantly or entirely, essentially straight; and/or
    wherein the at least one slit within extends at least until the cup base; and/or
    wherein the at least one slit within extends at least sectionally in the direction of oscillations of the measuring tube relative to the counteroscillator; and/or
    wherein also the cup base is slit; and/or
    wherein the at least one slit extends at least sectionally also along the cup base, especially in the direction of a radius of the cup base.

7. Measuring transducer as claimed in claim 1, wherein the at least one slit extends to a free edge of the magnet cup, especially a free edge essentially facing the counteroscillator.

8. Measuring transducer as claimed in claim 7, wherein the at least one slit extends along the cup wall, starting from the free edge of the magnet cup, especially the free edge facing the counteroscillator, at least to the cup base.

9. Measuring transducer as claimed in claim 1, wherein also the permanent magnet of the at least one oscillation sensor has at least one slit, especially a slit extending at least sectionally in the direction of oscillations of the measuring tube relative to the counteroscillator.

10. Measuring transducer as claimed in claim 9, wherein the at least one slit of the permanent magnet extends to a free edge of the permanent magnet essentially facing the counteroscillator.

11. Measuring transducer as claimed in claim 1, wherein the measuring tube is composed at least partially, especially predominantly or completely, of a material having a smaller magnetic conductivity than a material of which the counteroscillator is at least predominantly composed.

12. Measuring transducer as claimed in claim 1,
wherein the counteroscillator is composed, at least partially, especially predominantly or completely, of a magnetically conductive material; and/or
wherein the measuring tube is composed partially, especially predominantly or completely, of tantalum.

13. Measuring transducer as claimed in claim 1,
wherein the counteroscillator is composed, at least partially, especially predominantly or completely, of a magnetically conductive material having a relative permeability of at least 10, especially more than 100; and/or
wherein the measuring tube is composed partially, especially predominantly or completely, of zirconium.

14. Measuring transducer as claimed in claim 1,
wherein the counteroscillator is composed, at least partially, especially predominantly or completely, of steel, especially a free-machining steel or a structural steel; and/or
wherein the measuring tube is composed partially, especially predominantly or completely, of titanium.

15. Measuring transducer as claimed in claim 1, wherein the permanent magnet of the at least one oscillation sensor is composed, at least partially, especially predominantly or completely, of a rare earth alloy, especially AlNiCo, NyFeB, SmCo, or the like; and/or
wherein the permanent magnet of the at least one oscillation sensor is composed, at least partially, especially predominantly or completely, of ferrite; and/or
wherein the magnet cup of the at least one oscillation sensor is composed partially, especially predominantly or completely, of steel, especially a free-machining steel or a structural steel; and/or
wherein the magnet cup of the at least one oscillation sensor is composed partially, especially predominantly or completely, of ferrite; and/or
wherein the counteroscillator is composed partially, especially predominantly or completely, of steel, especially a free-machining steel or a structural steel; and/or
wherein the measuring tube is composed partially, especially predominantly or completely, of steel, especially stainless steel and/or austenitic steel, especially 316 L, 318 L, or a nickel alloy, especially Hastelloy.

16. Measuring transducer as claimed in claim 1, wherein the magnet cup of the first oscillation sensor includes at least two slits, especially more than two slits and/or slits extending essentially parallel to one another, at least within the cup wall and/or essentially uniform slits; and/or
wherein the magnet cup of the first oscillation sensor includes at least two slits, especially more than two slits, within the cup base, especially slits extending essentially radially and/or essentially uniform slits; and/or
wherein the permanent magnet of the first oscillation sensor includes at least two slits, especially more than two slits and/or slits extending essentially parallel to one another and/or essentially uniform slits.

17. Measuring transducer as claimed in claim 1, showing at least a first, natural oscillation mode, in which at least the measuring tube can execute bending oscillations in an imaginary primary oscillation plane.

18. Measuring transducer as claimed in claim 17, wherein the measuring tube is excited by means of the oscillation exciter, at least at times, in such a manner that it oscillates at least partially, especially predominantly or exclusively, in the imaginary, primary plane of oscillation.

19. Measuring transducer as claimed in claim 1, wherein the oscillation exciter is fed during operation, at least at times, with an electric driver signal effecting oscillations of the measuring tube, especially lateral, bending oscillations of the measuring tube in the imaginary, primary plane of oscillation.

20. Measuring transducer as claimed in claim 19, wherein the first oscillation sensor and the oscillation exciter are essentially of equal construction.

21. Measuring transducer as claimed in claim 1, wherein the oscillation exciter includes a coil.

22. Measuring transducer as claimed in claim 21, wherein the oscillation exciter further includes a permanent magnet magnetically coupled with the coil, wherein the permanent magnet is placed within a magnet cup composed at least partially of magnetically conductive material, and wherein the permanent magnet is held to a cup base, especially a cup base secured to the measuring tube.

23. Measuring transducer as claimed in the claim 22, wherein a cup wall of the magnet cup of the oscillation exciter, especially a circular-cylindrical and/or tubular, cup wall, extends from the cup base of the at least one oscillation exciter, especially in the direction of the counteroscillator, and includes at least one slit, especially a slit extending at least sectionally in the direction of oscillations of the measuring tube relative to the counteroscillator.

24. Measuring transducer as claimed in claim 23, wherein the coil of the oscillation exciter is mechanically connected with the counteroscillator, especially rigidly coupled.

25. Measuring transducer as claimed in claim 1, wherein the first oscillation sensor is placed on the inlet side of the measuring tube.

26. Measuring transducer as claimed in claim 25, further including a second oscillation sensor, especially a second oscillation sensor of essentially equal construction to that of the first oscillation sensor.

27. Measuring transducer as claimed in claim 26, wherein the second oscillation sensor is placed on the outlet side of the measuring tube.

28. Measuring transducer as claimed in claim 1, wherein the measuring tube is surrounded, at least partially, by the counteroscillator; and/or
wherein the counteroscillator is essentially tubular; and/or
wherein the counteroscillator is essentially straight.

29. Measuring transducer as claimed in claim 1, wherein the measuring tube is essentially straight.

30. Measuring transducer as claimed in claim 29, wherein also the counteroscillator is essentially tubular and essentially straight.

31. Measuring transducer as claimed in claim 30, wherein measuring tube and counteroscillator are directed essentially coaxially with respect to one another.

32. Measuring transducer as claimed in claim 31, wherein also the counteroscillator executes, at least at times during operation, bending oscillations about the bending oscillation axis.

33. Measuring transducer as claimed in claim 29, wherein the measuring tube executes during operation, at least at times, torsional oscillations about a torsional oscillation axis essentially parallel to, especially coincident with, the bending oscillation axis.

34. Measuring transducer as claimed in claim 1, wherein the measuring tube extends between the two coupling zones with essentially constant cross section, especially a constant cross section of circular shape; and/or wherein the measuring tube is formed essentially cylindrically, especially circular-cylindrically.

35. Measuring transducer as claimed in claim 1, wherein the measuring tube communicates with the pipeline via an inlet tube piece opening on the inlet-side and via an outlet tube piece opening on the outlet-side.

36. Measuring transducer as claimed in claim 35, further comprising a transducer housing affixed to the inlet tube piece and to the outlet tube piece.

37. Measuring transducer as claimed in claim 1, further comprising a transducer housing.

38. Use of a measuring transducer, as claimed in claim 1, in an in-line measuring device, especially a Coriolis mass flow measuring device, a density measuring device, a viscosity measuring device, or the like, for measuring and/or monitoring at least one parameter, especially a mass flow, m, a density, p, and/or a viscosity, n, of a medium flowing in a pipeline.

* * * * *